United States Patent
Croce et al.

(10) Patent No.: US 9,427,460 B2
(45) Date of Patent: Aug. 30, 2016

(54) USE OF MIR-494 TO MODULATE TRAIL-INDUCED APOPTOSIS THROUGH BIM DOWN-REGULATION

(71) Applicant: Ohio State Innovation Foundation, Columbus, OH (US)

(72) Inventors: Carlo M. Croce, Columbus, OH (US); Giulia Romano, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/429,856

(22) PCT Filed: Sep. 23, 2013

(86) PCT No.: PCT/US2013/061157
§ 371 (c)(1),
(2) Date: Mar. 20, 2015

(87) PCT Pub. No.: WO2014/047546
PCT Pub. Date: Mar. 27, 2014

(65) Prior Publication Data
US 2015/0238569 A1    Aug. 27, 2015

Related U.S. Application Data

(60) Provisional application No. 61/704,542, filed on Sep. 23, 2012.

(51) Int. Cl.
| | | |
|---|---|---|
| *C07H 21/02* | (2006.01) |
| *C07H 21/04* | (2006.01) |
| *C12N 15/85* | (2006.01) |
| *A61K 38/19* | (2006.01) |
| *A61K 38/17* | (2006.01) |
| *C12Q 1/68* | (2006.01) |
| *C12N 15/113* | (2010.01) |
| *A61K 31/713* | (2006.01) |
| *A61K 45/06* | (2006.01) |
| *A61K 31/7105* | (2006.01) |
| *G01N 33/574* | (2006.01) |
| *G01N 33/68* | (2006.01) |

(52) U.S. Cl.
CPC ............ *A61K 38/19* (2013.01); *A61K 31/713* (2013.01); *A61K 31/7105* (2013.01); *A61K 38/1761* (2013.01); *A61K 45/06* (2013.01); *C12N 15/1135* (2013.01); *C12Q 1/6886* (2013.01); *G01N 33/574* (2013.01); *G01N 33/6863* (2013.01); *C12N 2310/113* (2013.01); *C12N 2310/14* (2013.01); *C12Q 2600/106* (2013.01); *C12Q 2600/136* (2013.01); *C12Q 2600/158* (2013.01); *C12Q 2600/16* (2013.01); *C12Q 2600/178* (2013.01); *G01N 2800/52* (2013.01)

(58) Field of Classification Search
CPC . A61K 48/00; C12N 2310/11; C12N 15/113
See application file for complete search history.

(56) References Cited

PUBLICATIONS

J Immunol, Jun. 1, 2012;188(11), 5500-10.*
Mol Cancer Ther. Dec. 2009;8(12):3173-80.*
Life Sci. Jan. 30, 2010;86(5-6):192-8.*

* cited by examiner

*Primary Examiner* — Amy Bowman
(74) *Attorney, Agent, or Firm* — MacMillan, Sobanski & Todd, LLC

(57) ABSTRACT

Methods and compositions for inhibiting tumorigenicity both in vitro and in vivo in a subject in need thereof, comprising administering an effective amount of an anti-miR-494 nucleic acid construct sufficient to target one or more tumor suppressor genes (TSGs) are described. Activation of the ERK1/2 pathway is a major determinant of diverse cellular processes and cancer development and is responsible for the transcription of several important miRNAs. Described herein is a link between the ERK1/2 pathway and BIM expression through miR-494. This ERK1/2 pathway regulates apoptosis and cell proliferation through miR-494 and mechanisms responsible for TRAIL resistance. Materials and methods related to the study and treatment of cancer are described.

3 Claims, 16 Drawing Sheets
(15 of 16 Drawing Sheet(s) Filed in Color)

| miRNA | fold change |
|---|---|
| hsa-miR-494 | -8.92 |
| hsa-miR-628-5p | -6.92 |
| hsa-miR-455-5p | -5.29 |
| hsa-miR-16 | -5.15 |
| hsa-miR-548b-5p | -5.14 |
| hsa-miR-194 | -5.10 |
| hsa-miR-342-3p | -4.54 |
| hsa-miR-489 | -4.02 |
| hsa-miR-19b | -3.76 |

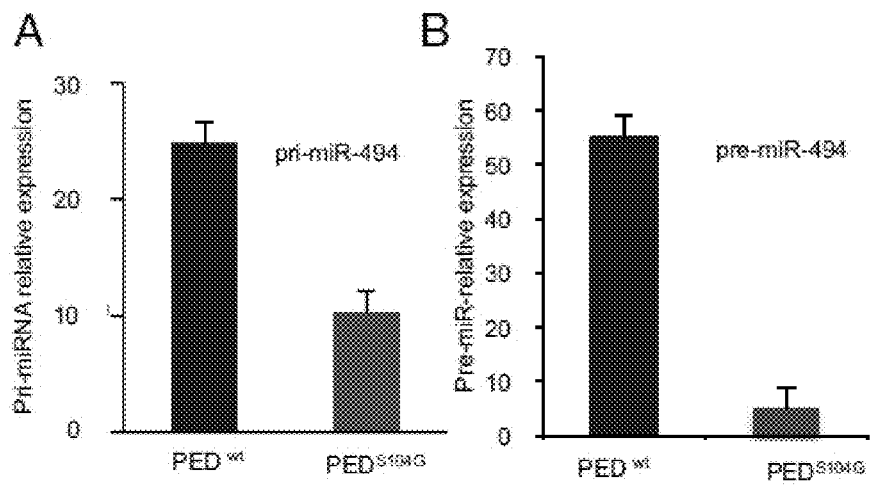
FIG. 2A  FIG. 2B
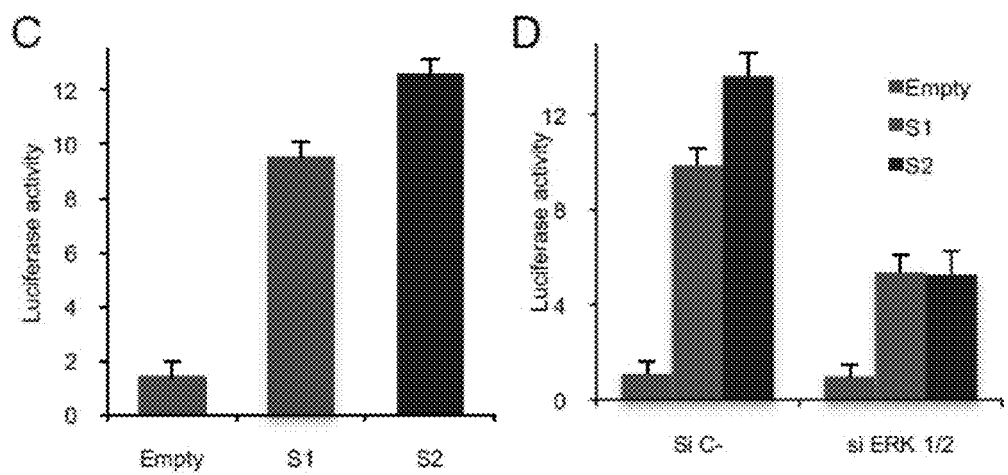
FIG. 2C  FIG. 2D

A
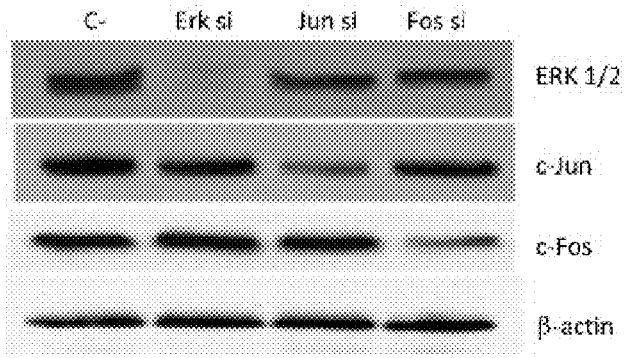
FIG. 7A
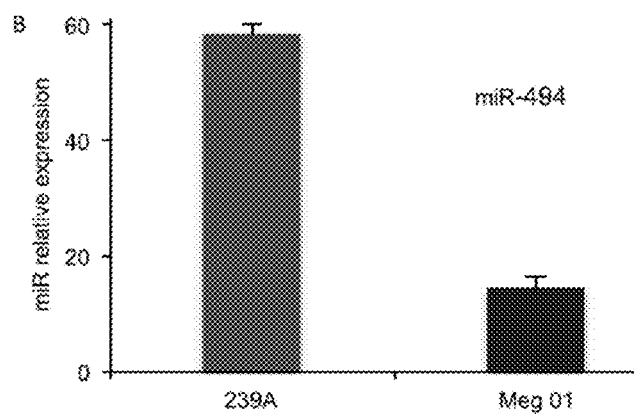
FIG. 7B
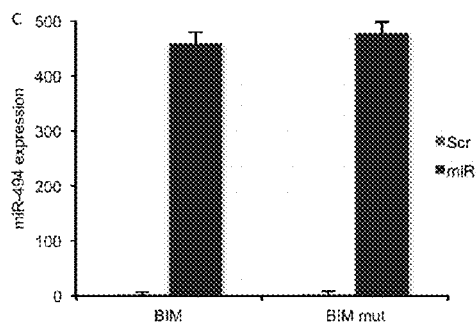 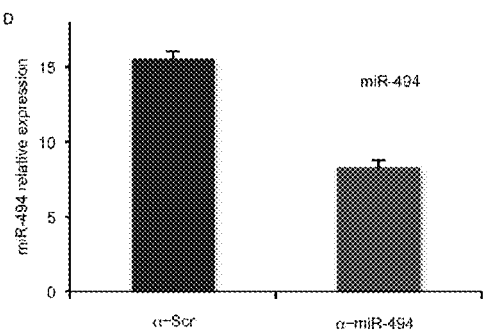
FIG. 7C          FIG. 7D

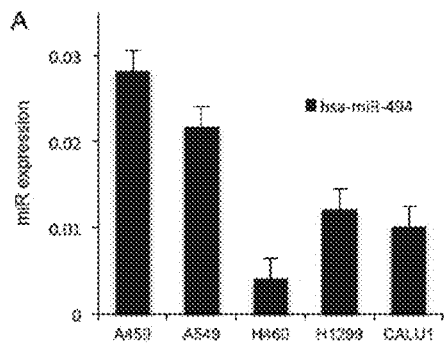 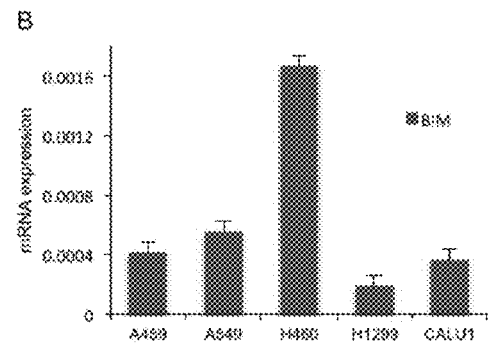
FIG. 8A  FIG. 8B
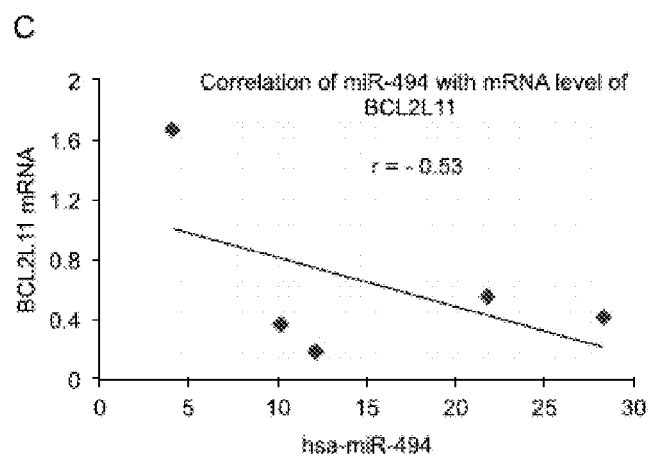
FIG. 8C
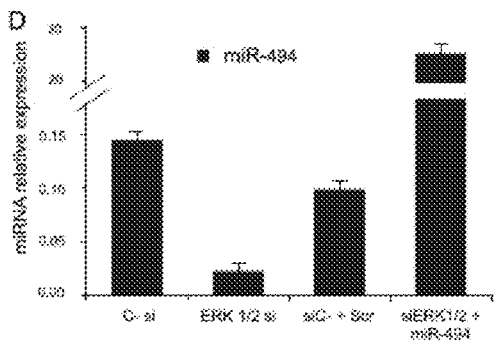 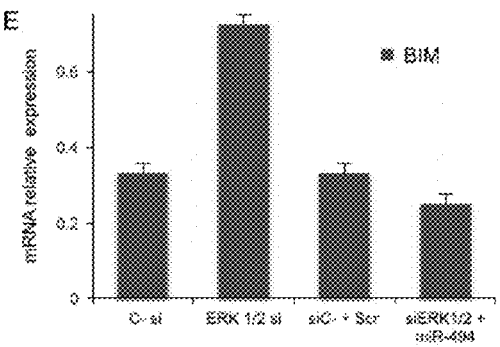
FIG. 8D  FIG. 8E

SEQUENCE LISTING

<160> NUMBER OF SEQ ID NOS: 16

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctagagagc caaatgtctg tgtgcaa                                        27

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctagagagt gggagacagg gatgttaat                                      29

```
<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgtgtgatg tgtcctacta atgctgtaac ttgtag                             36

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctacaagtta cagcattagt aggacacatc acacagt                            37

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtacctcat catccccacc taacgtagc                                     29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagcttcgtg agaacaccag tgagagatg                                     29

<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
guccuacugu uucau                                                    15

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtaccgtcg aagtcatgca tatgcatcg                                     29

<210> SEQ ID NO 9
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagcttggta aattgtagtg ctgtgttgct c                                      31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgcattaat ttaaaagctc tcaaatggat g                                      31

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacaagaaat ggtcagtgtg aggcat                                            26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgatcgttg tagagcatca ggcctt                                            26

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatgaactct caatttggat caaacccg                                          28

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gttgggtggt tcatttaagg gtattcctga                                        30

<210> SEQ ID NO 15
<211> LENGTH: 30
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcatcaatgg gagaataatt taatcagctc                                          30

<210> SEQ ID NO 16
<211> LENGTH: 13
<212> TYPE: RNA
<213> ORGANISM: Homo sapiens

<400> SEQUENCE: 16
ugaaacauac acg                                                            13
```

USE OF MIR-494 TO MODULATE TRAIL-INDUCED APOPTOSIS THROUGH BIM DOWN-REGULATION

CROSS-REFERENCE TO RELATED APPLICATIONS

This application claims the benefit of the PCT/US2010/057758 application filed Sep. 23, 2013, which claims priority to the U.S. Provisional Application No. 61/704,542, filed Sep. 23, 2012, the entire disclosure of which is expressly incorporated herein by reference for all purposes.

SEQUENCE LISTING

The instant application contains a Sequence Listing which has been submitted via EFS-web and is hereby incorporated by reference in its entirety. The ASCII copy, created on Sep. 19, 2013, is named 604_54418_SEQ_LIST_13072.txt, and is 3,838 bytes in size.

BACKGROUND

MicroRNAs (miRNAs or miRs) have an important role in the development of chemosensitivity or chemoresistance in different types of cancer. Activation of the ERK1/2 pathway is a major determinant of diverse cellular processes and cancer development and is responsible for the transcription of several important miRNAs. MiRNAs are attractive drug targets because they regulate expression of many cellular proteins and are often differentially expressed in malignant versus normal cells.

TNF-related apoptosis-inducing ligand (TRAIL) in an apoptosis-inducing cytokine. TRAIL is a promising apoptosis-based antitumor agent. However, many human cancer cells remain resistant to TRAIL-induced apoptosis.

While many therapeutic approaches to cancer treatment have been suggested, there exists a need for additional efficacious anti-cancer agents and vectors. Methods and materials for effective and safe anti-cancer treatments in vivo are needed. Improved understanding of the biochemical pathways involved in drug resistance and methods of drug discovery are needed. Further, there remains an unmet medical need for developing gene therapy vectors, having enhanced therapeutic activity, minimized toxicity, and a broad target range for treating neoplastic disorders.

SUMMARY OF THE INVENTION

In a first broad aspect, described herein is the use of an anti-miR-494 as a therapeutic to induce apoptosis. In another broad aspect, described herein is the use of an anti-miR-494 as a therapeutic to increase drug sensitivity.

In another broad aspect, described herein is the co-administering of an anti-miR-494 and TRAIL as chemotherapeutic (i.e., anti-miR-494 will decrease TRAIL resistance).

In another broad aspect, described herein is the use of anti-miR-494 to regulate expression of BIM in order to promote apoptosis of a tumor cells, such as, but not limited to, lung cancer, breast cancer, osteosarcoma, gastrointestinal tumors and melanoma.

In another broad aspect, described herein is the use of miR-494 to target BIM 3' UTR.

In another broad aspect, described herein a method for restoring a desired pattern of ERK1/2 activity in a subject in need thereof, comprising administering an effective amount of at least one anti-miR-494 sufficient to target one or ERK1/2.

In another broad aspect, described herein a method for inducing re-expression of a tumor suppressor gene (TSG) in a subject in need thereof, comprising administering an effective amount of an anti-miR-494 sufficient to induce TSG expression.

In certain embodiments, the TSG comprises one or more of BIM and TRAIL.

In another broad aspect, described herein a method for inhibiting tumorigenicity both in vitro and in vivo in a subject in need thereof, comprising administering an effective amount of an anti-miR-494 nucleic acid construct sufficient to target one or more tumor suppressor genes (TSGs). In certain embodiments, the subject is a cancer patient. In certain embodiments, the inhibiting method includes epigenetic regulation of non-small cell lung cancer (NSCLC).

In another broad aspect, described herein a method for increasing expression of a tumor suppression gene (TSG), the method comprising: transfecting a cell with an anti-mir-494 nucleic acid construct. In certain embodiments, the TSG comprises one or more of BIM and TRAIL.

In another broad aspect, described herein a method for up-modulating expression levels of BIM and/or TRAIL in a cell, comprising transfecting the cell with an anti-miR-494 nucleic acid construct.

In another broad aspect, described herein a method for inhibiting tumorigenicity both in vitro and in vivo comprising inhibiting expression of miR-494 in a cancer cell.

In another broad aspect, described herein a method for developing an epigenetic therapy using synthetic anti-miR-494, alone or in combination with other treatments, to reactivate tumor suppressors and normalize aberrant patterns of BIM and/or TRAIL expression in a cancer cell. In certain embodiments, the cell is a cancer cell, such as a lung cancer, a breast cancer, an osteosarcoma and a melanoma.

In another broad aspect, described herein a method of inhibiting tumorigenesis in a subject who has, or is suspected of having, a cancer-related disease in which at least miR-494 is up-regulated in the cancer cells of the subject, relative to control cells, comprising: when the miR-494 is up-regulated in the cancer cells, administering to the subject an effective amount of at least one compound for inhibiting expression of the miR-494, such that tumorigenesis is inhibited in the subject.

In certain embodiments, the compound comprises and anti-miR-494 nucleic acid construct, or isolated variants or biologically-active fragments or functional equivalents thereof, or antibodies that bind thereto.

In certain embodiments, a method of treating a cancer cell or inhibiting down-regulation of BIM includes measuring a miR-494 expression level in the cancer cell prior to administering TRAIL and anti-miR-494; classifying the cancer cell as over-expressing miR-494 if the miR-494 level is 2-12 fold higher than a control level; and administering an inhibitor of miR-494 in an amount sufficient to reduce miR-494 levels. In certain embodiments, the miR-494 level is reduced by at least 25% after administration of the miR-494 inhibitor. In certain embodiments, the miR-494 level is reduced by 25-50%. In certain embodiments, the miR-494 level after administration of the therapy is less than 5 fold higher than a control level. In certain embodiments, the miR-494 level after administration of the therapy is less than 2 fold higher than a control level. In certain embodiments, the miR-494 level in the treated cell, after administration of the therapy, is within 25% of a non-cancerous control level.

In another broad aspect, described herein a method of identifying an inhibitor of tumorigenesis, comprising: providing a test agent to a cell, and measuring the level of at least miR-494 associated with an altered expression level in a cancer-related disease, wherein an increase or decrease in the level of miR-494 in the cell, relative to a suitable control cell, is indicative of the test agent being an inhibitor of tumorigenesis. In certain embodiments, the cancer is a lung cancer.

In another broad aspect, described herein a pharmaceutical composition for treating a cancer-related disease, comprising: at least an anti-miR-494 nucleic acid construct and a pharmaceutically-acceptable carrier. In certain embodiments, the cancer-related disease is a lung cancer.

In another broad aspect, described herein a method for inducing apoptosis of a cancer cell, the method comprising contacting the cancer cell with an agent that inhibits the ERK1/2 signaling pathway in the cancer cell. In certain embodiments, the cell is present in a subject. In certain embodiments, the cell does not over-express miR-494.

In certain embodiments, the agent is an organic compound that specifically inhibits the ERK1/2 signaling pathway and causes down-regulation of miR-494.

In certain embodiments, the compound comprises: a death effector domain-containing protein, such as phosphoprotein enriched in diabetes (PED) or phosphoprotein enriched in astrocytes (PEA-15).

In certain embodiments, the agent is a nucleic acid agent that specifically antagonizes the ERK1/1 signaling pathway.

In certain embodiments, the agent is selected from the group consisting of a short interfering RNA (siRNA), a short hairpin RNA (shRNA), a microRNA (miRNA), an antisense nucleic acid, and a complementary DNA (cDNA).

In certain embodiments, the miRNA agent comprises an anti-miR-494 nucleic acid construct.

In another broad aspect, described herein a method for treating or ameliorating a cancer in a subject, the method comprising administering to the subject a pharmaceutical composition comprising an effective amount of an agent which down-regulates ERK1/2 signaling pathway and down-regulates the expression of miR-494.

In certain embodiments, the agent is an organic compound that specifically inhibits the ERK1/2 signaling pathway. In certain embodiments, the compound comprises: a death effector domain-containing protein, such as phosphoprotein enriched in diabetes (PED) or phosphoprotein enriched in astrocytes (PEA-15).

In another broad aspect, described herein a method of treating or inhibiting cellular proliferation in a subject in need thereof comprising administering to the subject an inhibitor of miR-494. In certain embodiments, the inhibitor of miR-494 is an antisense oligonucleotide having a sequence that is at least partially complementary to: a mature miR-494 sequence, a pri-miR-494 and/or a pre-miR-494. In certain embodiments, the inhibitor of miR-494 is an antisense oligonucleotide having a sequence that is, or is at least partially complementary to, a miR-494 transcriptional promoter sequence, such as (S1) and/or (S2). In certain embodiments, the antisense oligonucleotide comprises at least one sugar and/or backbone modification.

In certain embodiments, the inhibitor is administered to the subject by an intravenous or subcutaneous route of administration.

In certain embodiments, apoptosis of cancer cells is increased in the subject following administration of the inhibitor as compared to an untreated subject.

In certain embodiments, the expression of BIM is increased in the subject following administration of the inhibitor as compared to an untreated subject. In certain embodiments, the subject is a human.

In another broad aspect, described herein a construct comprising an anti-miR-494 nucleic acid and at least one inducer of apoptosis.

In certain embodiments, the inducer of apoptosis is selected from BIM and TRAIL.

In certain embodiments, the anti-miR-494 nucleic acid is a variant of a native miR-494, pri-miR-494 and/or pri-miR-494, or a homolog, analog and/or fragment thereof.

In certain embodiments, the anti-miR-494 nucleic acid is substantially a nucleic acid sequence corresponding to or complementary to a form of miR-494 selected from the group consisting of: a primary transcript of miR-494 (pri-miR-494); a precursor of miR-494 (pre-miR-494); an RNA duplex of miR-494, and a mature miR-494.

In another broad aspect, described herein a vector comprising the nucleic acid construct as described herein.

In another broad aspect, described herein an isolated host cell comprising the vector as described herein.

In another broad aspect, described herein a pharmaceutical composition comprising as an active ingredient the construct, and at least one pharmaceutically acceptable carrier, excipient or diluent.

In another broad aspect, described herein a method for treating cancer in a human subject, comprising administering to a human subject in need thereof a therapeutically effective amount of the construct, thereby treating cancer in the human subject.

In another broad aspect, described herein a method for inhibiting tumor progression in a human subject, comprising administering to a human subject in need thereof a therapeutically effective amount of the construct, thereby inhibiting tumor progression in the human subject.

In another broad aspect, described herein a method for reducing or alleviating a symptom associated with a neoplastic disorder in a human subject, comprising administering to a human subject in need thereof a therapeutically effective amount of the construct, thereby reducing or alleviating a symptom associated with a neoplastic disorder in the human subject.

In certain embodiments, the subject is afflicted with a tumor characterized by endogenous expression of miR-494 in at least a portion of the cells of the tumor. In certain embodiments, the subject is afflicted with a cancer selected from lung cancer, breast cancer, osteosarcoma, gastrointestinal tumors, and melanoma.

In certain embodiments, the administering is carried out by a route selected from the group consisting of injection, infusion and direct injection into the tumor.

In certain embodiments, the method is carried out in addition to administering a chemotherapeutic agent to the subject.

In another broad aspect, described herein a kit comprising i) one or more dosage units of the construct; and ii) instructions for administering the construct to a subject in need thereof.

In another broad aspect, described herein a method of affecting a cell by inhibiting proliferation of the cell and/or inducing apoptosis of the cell, the method comprising introducing an effective amount of a miR-specific inhibitor of at least miR-494 into the cell. In certain embodiments, the cell is a mammalian cell. In certain embodiments, the cell is a cancer cell.

In certain embodiments, the miR-specific inhibitor is selected from the group consisting of anti-miRs and target mimics.

In certain embodiments, the miR-specific inhibitor comprises a nucleotide sequence of least 6 consecutive nucleotides that are complementary to the miR-494, and has at least 50% complementarity to the rest of the miR-494 sequence, and wherein the miR-specific inhibitor of miR-494 induce expression of at least one of BIM and TRAIL in the cell.

In certain embodiments, the miR-specific inhibitor of miR-494 up-regulates one or more of BIM and TRAIL.

In certain embodiments, the miR-specific inhibitor has at least 60% complementarity to anti-miR-494.

In certain embodiments, the miR-specific inhibitor has at least 70% complementarity to anti-miR-494.

In certain embodiments, the miR-specific inhibitor has at least 80% complementarity to anti-miR-494.

In certain embodiments, the miR-specific inhibitor has at least 90% complementarity to anti-miR-494.

In certain embodiments, the miR-specific inhibitor is chemically modified on at least one nucleotide.

In another broad aspect, described herein a method of up-regulating BIM and/or TRAIL in a mammalian cell comprising introducing into the mammalian cell an effective amount of a miR-specific inhibitor of at least miR-494 into the mammalian cell. In certain embodiments, the mammalian cell is a cancer cell. In certain embodiments, the miR-specific inhibitor is selected from the group consisting of anti-miR and target mimics.

In certain embodiments, the miR-specific inhibitor comprises a nucleotide sequence of least 6 consecutive nucleotides that are complementary to the miR-494, and has at least 50% complementarity to the rest of the miR-494 sequence, and wherein the miR-specific inhibitor of miR-494 induce expression of at least one of BIM and TRAIL in the cell.

In another broad aspect, described herein a method for determining the cell cycle progression phenotype of a cell sample obtained from a subject, comprising: a) measuring the level of at least miR-494 in the cell sample; and b) comparing the level of at least miR-494 with a cell cycle progression reference value, wherein a level greater than the cell cycle progression reference value is indicative of an accelerated cell cycle progression in the cell sample.

In certain embodiments, the cell cycle progression phenotype is proliferation. In certain embodiments, the cell cycle progression phenotype is apoptosis.

In another broad aspect, described herein a method of measuring proliferation in a neoplasm comprising determining the level of miR-494 in the neoplasm.

In another broad aspect, described herein a method of measuring proliferation is a subpopulation of cells in a neoplasm comprising determining the level of miR-494 in the subpopulation of cells.

In another broad aspect, described herein a method of diagnosing whether a neoplasm is resistant to standard chemotherapy, the method comprising: determining the level of at least one of miR-494 and TRAIL in the neoplasm, and identifying the neoplasm as chemotherapy resistant if the level of miR-494 is greater in the neoplasm and/or the level of TRAIL is less in the neoplasm than in a normal control.

In another broad aspect, described herein a method of determining whether a neoplasm comprises a subpopulation of cells resistant to standard chemotherapy, the method comprising: isolating the subpopulation of cells, determining the level of at least one of miR-494 and TRAIL in the subpopulation of cells, and identifying the subpopulation of cells as chemotherapy resistant if the level of miR-494 is greater in the subpopulation and/or the level of TRAIL is less in the subpopulation than in a normal control. In certain embodiments, the subpopulations of cells are stem-like cells. In certain embodiments, the normal control is bulk neoplastic cells.

Embodiments of the invention include methods of determining coverage or denial of health insurance reimbursement and/or payment for treatments for disease based on the result of diagnostic and prognostic methods described herein. For example, a method of excluding a treatment from insurance coverage, the method comprising: identifying a patient having health insurance; receiving a result of a diagnostic procedure on the patient, wherein the diagnostic procedure comprises determining whether a neoplasm is resistant to standard chemotherapy; and denying health insurance coverage for chemotherapy treatment if the level of miR-494 is high, as compared to control. In some embodiments, the chemotherapy is pre-operative and/or post-operative adjuvant therapy. In some embodiments, chemotherapy is contraindicated. In some instances the contraindicated chemotherapeutic is a small molecule to inhibit EGFR tyrosine kinase, such as: gefitinib, erlotinib, or lapatinib, or to inhibit the MAP Kinase pathway, such as sorafenib.

In another broad aspect, described herein a method of decreasing proliferation of a cell, comprising contacting the cell with an inhibitory nucleic acid complementary to miR-494, in an amount effective to decrease proliferation of the cell.

In another broad aspect, described herein a method of increasing the sensitivity of a cell to a chemotherapeutic agent, comprising contacting the cell with an inhibitory nucleic acid complementary to miR-494, in an amount effective to sensitize the cell to the chemotherapeutic agent.

In certain embodiments, the inhibitory nucleic acid is transfected into the cell.

In certain embodiments, the chemotherapeutic agent is an apoptosis regulator, such as, but not limited to, BIM and TRAIL.

In certain embodiments, the cell is a cancer stem cell.

In certain embodiments, the cell is a neoplastic cell.

In another broad aspect, described herein a method of treating a neoplasm in a subject, comprising administering to the subject an effective amount of an inhibitory nucleic acid that inhibits miR-494.

In certain embodiments, the method further comprises administering a second therapy, wherein administration of the inhibitory nucleic acid sensitizes the neoplasm to the second therapy. In certain embodiments, the second therapy comprises administering a chemotherapeutic agent.

In certain embodiments, the cancer is selected from the group consisting of: lung cancer, breast cancer, osteosarcoma, gastrointestinal tumors and melanoma.

In another broad aspect, described herein a kit for analysis of a pathological sample, the kit comprising in a suitable container an RNA hybridization or amplification reagent for determining the level of miR-494, the levels of one or more of BIM and TRAIL, and directions for use.

In another broad aspect, described herein a pharmaceutical composition comprising substantially purified anti-miR-494 and a pharmaceutically acceptable carrier.

In another broad aspect, described herein a pharmaceutical composition comprising substantially purified anti-miR-494 and TRAIL, and a pharmaceutically acceptable carrier.

In another broad aspect, described herein a method which further comprises measuring the level of at least one additional miR gene product in the test sample, wherein the miR is selected from the group shown in FIG. 1D.

In another aspect, described herein is a method for treating cancer in a human subject by administering a therapeutically effective amount of a nucleic acid construct, thereby treating cancer in the human subject.

In another aspect, described herein is a method for inhibiting tumor progression in a human subject, the method comprising administering to a human subject in need thereof a therapeutically effective amount of a nucleic acid construct, thereby inhibiting tumor progression in the human subject.

In another aspect, described herein is a method for inhibiting tumor metastasis in a human subject, the method comprising administering to a human subject in need thereof a therapeutically effective amount of a nucleic acid construct, thereby inhibiting tumor metastasis in the human subject.

In another aspect, described herein is a method for reducing or alleviating a symptom associated with a neoplastic disorder in a human subject, the method comprising administering to a human subject in need thereof a therapeutically effective amount of a nucleic acid construct, thereby reducing or alleviating a symptom associated with a neoplastic disorder in the human subject.

In another aspect, the subject is afflicted, in one embodiment, with a cancer, tumor or a neoplastic disorder characterized by endogenous expression of miR-494 in at least a portion of the cells thereof.

In particular embodiments, the administering is carried out by a route selected from the group consisting of injection, infusion and direct injection into the tumor.

In particular embodiments, the administering comprises administering a single dose or multiple doses of the nucleic acid construct.

In particular embodiments, the methods further comprise a step of determining the level of miR-494 activity in a biological sample e.g. cells or tissue, from the subject.

In another aspect, described herein is a use of a nucleic acid construct for the preparation of a medicament for treating cancer in a human subject.

In another aspect, described herein is a use of a nucleic acid construct of the invention for the preparation of a medicament for inhibiting tumor progression in a human subject.

In another aspect, described herein is a use of a nucleic acid construct for the preparation of a medicament for inhibiting tumor metastasis in a human subject.

In another aspect, described herein is a use of a nucleic acid construct of the invention for the preparation of a medicament for reducing or alleviating a symptom associated with a neoplastic disorder.

In another aspect, described herein is a kit containing i) one or more dosage units of a nucleic acid construct sufficient for one or more courses of treatment for a cancer, tumor or neoplasm expressing miR-494; and ii) instructions for administering the nucleic acid construct to a subject in need thereof. The compositions, methods and kits are useful in the treatment of a variety of cancers and neoplastic disorders associated with expression of miR-494. In a particular embodiment, the cancer is selected from the group consisting of a sarcoma, a carcinoma, an adenocarcinoma, a lymphoma, and a leukemia. In a particular embodiment, the cancer is a lung cancer.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A: Western blot showing the expression of $PED^{WT}$ and $PED^{S104G}$ cells;

FIG. 1B: Western blot showing the different subcellular localization of ERK1/2 after empty vector, $PED^{WT}$, and $PED^{S104G}$ transfection in 293A cells;

FIG. 1C: Unsupervised hierarchical clustering based on miRNA expression profiles in $PED^{WT}$ versus $PED^{S104G}$ in 293A cells at a P value <0.05; and, FIG. 1D: Fold changes of microRNAs deregulated after $PED^{WT}$ versus $PED^{S104G}$ transfection are shown (P<0.05).

FIGS. 2A-2G. Identification of miR494 promoter:

FIG. 2A: qRT-PCRs showing pri-miR-494 down-regulation in 293A cells after $PED^{WT}$ and $PED^{S104G}$ transfection;

FIG. 2B: qRT-PCRs showing premiR-494 down-regulation in 293A cells after $PED^{WT}$ and $PED^{S104G}$ transfection;

FIG. 2C: Luciferase assays were carried out to identify the miR-494 promoter;

FIG. 2D: ERK regulation on miR-494 expression;

FIG. 2E: miR-494 promoter putative sequences (S1 and S2) were regulated by AP-1.

FIG. 2F: Chromatin immunoprecipitation analysis on S1 and S2 fragment. Chromatin was immunoprecipitated with c-Jun antibody; and FIG. 2G: A 30-kb genomic region spanning pri-miR-494: The schematic diagram represents two putative AP1 binding sequences (green rectangles) located 27.8 kb and 18.6 kb upstream of pri-miR-494. Data are presented as ±SD.

FIG. 3A: BIM 3' UTR contains one predicted miR494 binding site; the alignment of the seed regions of miR-494 [SEQ ID NO:16] with BIM 3' UTR [SEQ ID NO:7] is shown; the site of target mutagenesis is indicated in red;

FIG. 3B: Luciferase assays were carried out with pGL3-BIM luciferase constructs containing wild type (left side of the histograms) or mutated (right side of the histograms); relative repression of firefly luciferase expression was standardized to a transfection control; the reporter assays were performed three times with essentially identical results;

FIG. 3C: miR-494 down-regulation increases endogenous levels of BIM protein in 293A cells; and, FIG. 3D: qRT-PCR in 293A cells showing an increase in BIM expression after down-regulation of miR-494. Data are presented as ±SD.

FIG. 4A: Western blot showing the expression of BIM after $PED^{WL}$ and $PED^{S104G}$ transfection;

FIG. 4B: Western blot showing the expression of BIM, ERK1/2, p-ERK1/2 and p-Elk1 after transfection of either scrambled or miR-494 for 48 h and a time course of ERK1/2 inhibitor (ERK Inhibitor II FR180204);

FIG. 4C: qRT-PCR of miR-494 expression related to FIG. 4B;

FIG. 4D: qRT-PCR in 293A cells showing miR-494 down-regulation after interference of ERK1/2 signaling; and, FIG. 4E: qRT-PCR in 293A cells showing BIM increase after interference of AP1. Data are presented as ±SD.

FIG. 5A: Western blot showing the expression of BIM after miR494 transfection in H460 cells;

FIG. 5B: Western blot showing the expression of BIM after anti-miR-494 transfection in A549 cells;

FIG. 5C: Western blot showing the expression of BIM and ERK1/2 after ERK1/2 silencing and miR-494-enforced expression;

FIG. 5D: Western blot showing the expression of BIM, ERK1/2, c-Jun, and c-Fos after transfection of ERK1/2, c-Jun, and c-Fos siRNAs in A549 cells;

FIG. 5E: Percent cell proliferation assay on H460 cells after miR-494 or BIM siRNA and TRAIL treatment (200 ng/mL). Significance values of P<0.05 relative to untreated H460 cells;

FIG. 5F: Caspase 3/7 activity assay on H460 cells after miR-494 or BIM siRNA and TRAIL treatment (200 ng/mL). Significance values of P<0.05 relative to untreated H460 cells; and FIG. 5G: Western blot showing PARP and PARP cleaved expression after miR-scrambled, miR-494, siRNA control (Ctr), and siBIM in H460 cells treated with (200 ng/mL) TRAIL for 40 min Data are presented as ±SD.

FIGS. 6A-6D. Effects of miR-494 on tumorigenicity in vivo:

FIG. 6A and FIG. 6B: Clonogenic assays on H460 cells infected with control (empty) or miR-494 lentiviruses (miR-494). The clonogenic assays were performed three times. Representative plates are shown. Columns indicate number of clones derived from 500 cells plated;

FIG. 6C: Comparison of tumor engraftment sizes in nude mice injected with H460 cells stable infected with empty vector or miR-494; and, FIG. 6D: Summary diagram of system: PED$^{104}$ blocking ERK1/2 nuclear pathway down-regulates miR-494 increased sensitivity to apoptotic stimuli. Data are presented as ±SD.

FIG. 7A: Western blot showing protein expression after ERK1/2, c-Fos, and c-JUN siRNAs transfection.

FIG. 7B: qRT-PCR performed on Meg01 and 293A cells showing miR-494 endogenous level.

FIG. 7C: qRT-PCR performed on Meg01cells after enforced expression of miR-494.

FIG. 7D: qRT-PCR performed on 293A cells after miR-494 down-regulation as control of FIG. 3D.

FIG. 8A and FIG. 8B: qRT-PCR in NSCLC cells showing BIM and miR-494 expression in these cell lines. miR-494 was inversely related to BIM mRNA expression in the different NSCLC.

FIG. 8C: XY scatter plot showing inverse correlation between BIM and miR-494 in NSCLC cells.

FIG. 8D: qRT-PCR in A549 cells showing miR-494 downregulation after ERK1/2 siRNA with or without miR-494 over-expression.

FIG. 8E: qRT-PCR in A549 cells showing an increase in BIM expression after ERK1/2 siRNA with or without miR-494 over-expression.

DETAILED DESCRIPTION OF THE PREFERRED EMBODIMENT(S)

Figure 1A:
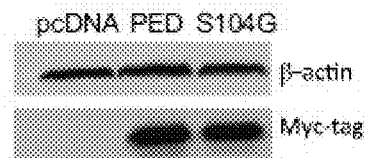
FIGS. 1A-1D. ERK1/2 regulation on miRNAs.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

DEFINITIONS

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The terms "miR," "mir" and "miRNA" generally refer to microRNA, a class of small RNA molecules that are capable of modulating RNA translation (see, Zeng and Cullen, RNA, 9(1):112-123, 2003; Kidner and Martiensen Trends Genet, 19(1):13-6, 2003; Dennis C, Nature, 420(6917):732, 2002; Couzin J, Science 298(5602):2296-7, 2002, each of which is incorporated by reference herein).

It is understood that a miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment.

Clinical outcome: Refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Cytokines: Proteins produced by a wide variety of hematopoietic and non-hematopoietic cells that affect the behavior of other cells. Cytokines are important for both the innate and adaptive immune responses.

Decrease in survival: As used herein, "decrease in survival" refers to a decrease in the length of time before death of a patient, or an increase in the risk of death for the patient.

Detecting level of expression: For example, "detecting the level of miR or miRNA expression" refers to quantifying the amount of miR or miRNA present in a sample. Detecting expression of the specific miR, or any microRNA, can be achieved using any method known in the art or described herein, such as by qRT-PCR. Detecting expression of miR includes detecting expression of either a mature form of miRNA or a precursor form that is correlated with miRNA expression. Typically, miRNA detection methods involve sequence specific detection, such as by RT-PCR. miR-specific primers and probes can be designed using the precursor and mature miR nucleic acid sequences.

MicroRNA (miRNA): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially-complementary to one or more messenger RNA molecules, and their primary function is to down-regulate gene expression. MicroRNAs regulate gene expression through the RNAi pathway.

miR expression: As used herein, "low miR expression" and "high miR expression" are relative terms that refer to the level of miRNAs found in a sample. In some embodiments, low and high miR expression is determined by comparison of miRNA levels in a group of control samples and test samples. Low and high expression can then be assigned to each sample based on whether the expression of miRNA in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miRNA, or both.

Subject: As used herein, the term "subject" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

Preventing, treating or ameliorating a disease: "Preventing" a disease refers to inhibiting the full development of a disease. The terms "prevent," "preventing" and "prevention" generally refer to a decrease in the occurrence of disease or disorder in a subject. The prevention may be complete, e.g., the total absence of the disease or disorder in the subject. The prevention may also be partial, such that the occurrence of the disease or disorder in the subject is less than that which would have occurred without the present invention. "Preventing" a disease generally refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that affect such disease. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

As used herein, a "candidate agent" is a compound selected for screening to determine if it can function as a therapeutic agent. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically-effective amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

The term "pharmaceutically acceptable vehicles" generally refers to such pharmaceutically acceptable carriers (vehicles) as would be generally used. Remington's Pharmaceutical Sciences, by E. W. Martin, Mack Publishing Co., Easton, Pa., 20 Edition, describes compositions and formulations suitable for pharmaceutical delivery of one or more therapeutic compounds, molecules or agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The term "pharmaceutically acceptable salt" generally refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts. Examples of bases include, but are not limited to, alkali metal (e.g., sodium) hydroxides, alkaline earth metal (e.g., magnesium) hydroxides, ammonia, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as Na+, NH4+, and NW4+ (wherein W is a C1-4 alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound In some embodiments of the present methods, use of a control is desirable. In that regard, the control may be a non-cancerous cell/tissue sample obtained from the same patient, or a cell/tissue sample obtained from a healthy subject, such as a healthy tissue donor. In another example, the control is a standard calculated from historical values. Tumor samples and non-cancerous cell/tissue samples can be obtained according to any method. For example, tumor and non-cancerous samples can be obtained from cancer patients that have undergone resection, or they can be obtained by extraction using a hypodermic needle, by microdissection, or by laser capture. Control (non-cancerous) samples can be obtained, for example, from a cadaveric donor or from a healthy donor.

In some embodiments, miR expression is measured relative to certain small non-coding RNAs (ncRNAs) that are expressed both abundantly and stably, making them good endogenous control candidates.

In some embodiments, screening comprises contacting the candidate agents with cells.

The cells can be primary cells obtained from a patient, or the cells can be immortalized or transformed cells.

The candidate agents can be any type of agent, such as a protein, peptide, small molecule, antibody or nucleic acid. In some embodiments, the candidate agent is a cytokine. In some embodiments, the candidate agent is a small molecule. Screening includes both high-throughout screening and screening individual or small groups of candidate agents.

MicroRNA Detection

In some methods herein, it is desirable to identify miRNAs present in a sample.

The sequences of precursor microRNAs (pre-miRNAs) and mature miRNAs are publicly available, such as through the miRBase database, available online by the Sanger Institute (see Griffiths-Jones et al., Nucleic Acids Res. 36:D154-D158, 2008; Griffiths-Jones et al., Nucleic Acids Res. 34:D140-D144, 2006; and Griffiths-Jones, Nucleic Acids Res. 32:D109-D111, 2004). The sequences of the precursor and mature forms of the presently disclosed preferred family members are provided herein.

Detection and quantification of RNA expression can be achieved by any one of a number of methods well known in the art (see, for example, U.S. Patent Application Publication No. 2006/0211000 and U.S. Pat. No. 7,955,848, herein incorporated by reference). Using the known sequences for RNA family members, specific probes and primers can be designed for use in the detection methods described below as appropriate.

In some cases, the RNA detection method requires isolation of nucleic acid from a sample, such as a cell or tissue sample. Nucleic acids, including RNA and specifically miRNA, can be isolated using any suitable technique. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

In some embodiments, use of a microarray is desirable. A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs, for example (although these procedures can be used in modified form for any RNA analysis) can be accomplished according to any method known in the art (see, for example, PCT Publication No. WO 2008/054828; Ye et al., Nat. Med. 9(4):416-423, 2003; Calin et al., N. Engl. J. Med. 353(17):1793-1801, 2005; each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is then carried out.

There are several types of microarrays that can be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array can be hybridized with amplified PCR products of size-selected small RNAs from two samples to be compared (such as non-cancerous tissue and cancerous or sample tissue) that are labeled with two different fluorophores. Alternatively, total RNA containing the small RNA fraction (including the miRNAs) can be extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

In some embodiments, use of quantitative RT-PCR is desirable. Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

Various methods of screening candidate agents can be used to identify therapeutic agents for the treatment of disease. Methods of detecting expression levels of RNA and proteins are, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter cancer disease state(s) either directly or indirectly.

It will be understood in methods described herein that a cell or other biological matter such as an organism (including patients) can be provided a miRNA or miRNA molecule corresponding to a particular miRNA by administering to the cell or organism a nucleic acid molecule that functions as the corresponding miRNA once inside the cell. The form of the molecule provided to the cell may not be the form that acts a miRNA once inside the cell. Thus, it is contemplated that in some embodiments, biological matter is provided a synthetic miRNA or a nonsynthetic miRNA, such as one that becomes processed into a mature and active miRNA once it has access to the cell's miRNA processing machinery. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments that concern the use of synthetic miRNAs, the use of corresponding nonsynthetic miRNAs is also considered, and vice versa. It will be understand that the term "providing" an agent is used to include "administering" the agent to a patient.

In certain embodiments, methods also include targeting a miRNA to modulate in a cell or organism. The term "targeting a miRNA to modulate" means a nucleic acid will be employed so as to modulate the selected miRNA. In some embodiments, the modulation is achieved with a synthetic or non-synthetic miRNA that corresponds to the targeted miRNA, which effectively provides the targeted miRNA to the cell or organism (positive modulation). In other embodiments, the modulation is achieved with a miRNA inhibitor, which effectively inhibits the targeted miRNA in the cell or organism (negative modulation).

In some embodiments, the miRNA targeted to be modulated is a miRNA that affects a disease, condition, or pathway. In certain embodiments, the miRNA is targeted because a treatment can be provided by negative modulation of the targeted miRNA. In other embodiments, the miRNA is targeted because a treatment can be provided by positive modulation of the targeted miRNA.

In certain methods, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like decrease in cell viability). Consequently, in some methods there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as preventatively, particularly in a patient identified to be potentially in need of the therapy or at risk of the condition or disease for which a therapy is needed.

In addition, certain methods concern employing one or more nucleic acids corresponding to a miRNA and a therapeutic drug. The nucleic acid can enhance the effect or efficacy of the drug, reduce any side effects or toxicity, modify its bioavailability, and/or decrease the dosage or frequency needed. In certain embodiments, the therapeutic drug is a cancer therapeutic. Consequently, in some embodiments, there is a method of treating cancer in a patient comprising administering to the patient the cancer therapeutic and an effective amount of at least one miRNA molecule that improves the efficacy of the cancer therapeutic or protects non-cancer cells. Cancer therapies also include a variety of combination therapies with both chemical and radiation based treatments.

Inhibitors of miRNAs can be given to achieve the opposite effect as compared to when nucleic acid molecules corresponding to the mature miRNA are given. Similarly, nucleic acid molecules corresponding to the mature miRNA can be given to achieve the opposite effect as compared to when inhibitors of the miRNA are given. For example, miRNA molecules that increase cell proliferation can be provided to cells to increase proliferation or inhibitors of such molecules can be provided to cells to decrease cell proliferation. For example, these embodiments can be contemplated in the context of the different physiological effects observed with the different miRNA molecules and miRNA inhibitors disclosed herein. These include, but are not limited to, the following physiological effects: increase and decreasing cell proliferation, increasing or decreasing apoptosis, increasing transformation, increasing or decreasing cell viability, reduce or increase viable cell number, and increase or decrease number of cells at a particular phase of the cell cycle. Methods are also contemplated to include providing or introducing one or more different nucleic acid molecules corresponding to one or more different miRNA molecules. It is contemplated that the following, at least the following, or at most the following number of different nucleic acid molecules may be provided or introduced: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or any range derivable therein. This also applies to the number of different miRNA molecules that can be provided or introduced into a cell.

General Description

It is to be understood that both the foregoing general description and the following detailed description are exemplary and explanatory only and are not intended to limit the scope of the current teachings. In this application, the use of the singular includes the plural unless specifically stated otherwise. In order to facilitate review of the various embodiments of the disclosure, the following explanations of specific terms are provided.

"miRNA nucleic acid" generally refers to RNA or DNA that encodes a miR as defined above, or is complementary to a nucleic acid sequence encoding a miR, or hybridizes to such RNA or DNA and remains stably bound to it under appropriate stringency conditions. Particularly included are genomic DNA, cDNA, mRNA, miRNA and antisense molecules, pri-miRNA, pre-miRNA, mature miRNA and miRNA seed sequences. Also included are nucleic acids based on alternative backbones or including alternative bases. MiRNA nucleic acids can be derived from natural sources or synthesized.

It is to be understood that a miRNAs or pre-miRNAs can be 18-100 nucleotides in length, and more preferably from 18-80 nucleotides in length. For example, mature miRNAs can have a length of 19-30 nucleotides, preferably 21-25 nucleotides, particularly 21, 22, 23, 24, or 25 nucleotides. MicroRNA precursors typically have a length of about 70-100 nucleotides and have a hairpin conformation. Thus, once a sequence of a miRNA or a pre-miRNA is known, a miRNA antagonist that is sufficiently complementary to a portion of the miRNA or the pre-miRNA can be designed according to the rules of Watson and Crick base pairing. As used herein, the term "sufficiently complementary" generally means that two sequences are sufficiently complementary such that a duplex can be formed between them under physiologic conditions. A miRNA antagonist sequence that is sufficiently complementary to a miRNA or pre-miRNA target sequence can be 70%, 80%, 90%, or more identical to the miRNA or pre-miRNA sequence. In one embodiment, the miRNA antagonist contains no more than 1, 2 or 3 nucleotides that are not complementary to the miRNA or pre-miRNA target sequence. In another embodiment, the miRNA antagonist is 100% complementary to a miRNA or pre-miRNA target sequence. Sequences for miRNAs are available publicly through the miRBase registry (Griffiths-Jones, et al., Nucleic Acids Res., 36(Database Issue):D154-D158 (2008); Griffiths-Jones, et al., Nucleic Acids Res., 36(Database Issue):D140-D144 (2008); Griffiths-Jones, et al., Nucleic Acids Res., 36(Database Issue):D109-D111 (2008)).

"MicroRNA seed sequence," "miRNA seed sequence," "seed region" and "seed portion" generally refer to nucleotides 2-7 or 2-8 of the mature miRNA sequence. The miRNA seed sequence is typically located at the 5' end of the miRNA.

A "miR-specific inhibitor" may be an anti-miRNA (antagomir or anti-miR) oligonucleotide. Anti-miRNAs may be single stranded molecules. Anti-miRs may comprise RNA or DNA or have non-nucleotide components. Anti-miRs anneal with and block mature microRNAs through extensive sequence complementarity. In some embodiments, an anti-miR may comprise a nucleotide sequence that is a perfect complement of the entire miRNA. In some embodiments, an anti-miR comprises a nucleotide sequence of at least 6 consecutive nucleotides that are complementary to the seed region of a microRNA molecule at positions 2-8 and has at least 50%, 60%, 70%, 80%, or 90% complementarity to the rest of the miRNA. In other embodiments, the anti-miR may comprise additional flanking sequence, complimentary to adjacent primary (pri-miRNA) sequences. Chemical modifications, such as 2'-O-methyl; locked nucleic acids (LNA); and 2'-O-methyl, phosphorothioate, cholesterol (antagomir); 2'-O-methoxyethyl can be used. Chemically modified anti-miRs are commercially available from a variety of sources, including but not limited to Sigma-Proligo, Ambion, Exiqon, and Dharmacon.

The miRNA antagonists can be oligomers or polymers of RNA or DNA, and can contain modifications to their nucleobases, sugar groups, phosphate groups, or covalent internucleoside linkages. In certain embodiment, modifications include those that increase the stability of the miRNA antagonists or enhance cellular uptake of the miRNA antagonists. In one embodiment, the miRNA antagonists are antagomirs, which have 2'-O-methylation of the sugars, a phosphorothioate backbone and a terminal cholesterol moiety.

In some embodiments, miR-specific inhibitors possess at least one microRNA binding site, mimicking the microRNA target (target mimics). These target mimics may possess at least one nucleotide sequence comprising 6 consecutive nucleotides complementary to positions 2-8 of the miRNA seed region. Alternatively, these target mimics may comprise a nucleotide sequence with complementarity to the entire miRNA. These target mimics may be vector encoded. Vector encoded target mimics may have one or more microRNA binding sites in the 5' or 3' UTR of a reporter gene. The target mimics may possess microRNA binding sites for more than one microRNA family. The microRNA binding site of the target mimic may be designed to mismatch positions 9-12 of the microRNA to prevent miRNA-guided cleavage of the target mimic.

In an alternative embodiment, a miR-specific inhibitor may interact with the miRNA binding site in a target transcript, preventing its interaction with a miRNA.

The terms "miRNA specific inhibitor" and "miRNA antagonist," generally refer to an agent that reduces or inhibits the expression, stability, or activity of a miRNA. A miRNA antagonist may function, for example, by blocking the activity of a miRNA (e.g., blocking the ability of a miRNA to function as a translational repressor and/or activator of one or more miRNA targets), or by mediating miRNA degradation. Exemplary miRNA antagonists include nucleic acids, for example, antisense locked nucleic acid molecules (LNAs), antagomirs, or 2'O-methyl antisense RNAs targeting a miRNA.

The phrase "inhibiting expression of a target gene" generally refers to the ability of an RNAi agent, such as a siRNA, to silence, reduce, or inhibit expression of a target gene. The another way, to "inhibit," "down-regulate," or "reduce," it is meant that the expression of the gene, or level of RNA molecules or equivalent RNA molecules encoding one or more proteins or protein subunits, or activity of one or more proteins or protein subunits, is reduced below that observed in the absence of the RNAi agent.

For example, in one embodiment, inhibition, down-regulation, or reduction contemplates inhibition of the target mRNA below the level observed in the presence of, for example, a siRNA molecule with scrambled sequence or with mismatches.

To examine the extent of gene silencing, a test sample (e.g., a biological sample from organism of interest expressing the target gene(s) or a sample of cells in culture expressing the target gene(s)) is contacted with a siRNA that silences, reduces, or inhibits expression of the target gene(s). Expression of the target gene in the test sample is compared to expression of the target gene in a control sample (e.g., a biological sample from organism of interest expressing the target gene or a sample of cells in culture expressing the target gene) that is not contacted with the siRNA. Control samples (i.e., samples expressing the target gene) are assigned a value of 100%. Silencing, inhibition, or reduction of expression of a target gene is achieved when the value of the test sample relative to the control sample is about 95%, 90%, 85%, 80%, 75%, 70%, 65%, 60%, 55%, 50%, 45%, 40%, 35%, 30%, 25%, 20%, 10% or 0%. Suitable assays include, e.g., examination of protein or mRNA levels using techniques known to those of skill in the art such as dot blots, northern blots, in situ hybridization, ELISA, microarray hybridization, immunoprecipitation, enzyme function, as well as phenotypic assays known to those of skill in the art.

An "effective amount" or "therapeutically effective amount" of a miR-specific inhibitor is an amount sufficient to produce the desired effect, e.g., inhibition of expression of a target sequence in comparison to the normal expression level detected in the absence of the miR-specific inhibitor Inhibition of expression of a target gene or target sequence by a miR-specific inhibitor is achieved when the expression level of the target gene mRNA or protein is about 90%, 80%, 70%, 60%, 50%, 40%, 30%, 25%, 20%, 15%, 10%, 5% or 0% relative to the expression level of the target gene mRNA or protein of a control sample. The desired effect of a miR-specific inhibitor may also be measured by detecting an increase in the expression of genes down-regulated by the miRNA targeted by the miR-specific inhibitor.

By "modulate" is meant that the expression of the gene, or level of RNA molecule or equivalent RNA molecules encoding one or more proteins or protein subunits, or activity of one or more proteins or protein subunits is up-regulated or down-regulated, such that expression, level or activity is greater than or less than that observed in the absence of the modulator. For example, the term "modulate" can mean "inhibit," but the use of the word "modulate" is not limited to this definition.

Non-limiting examples of suitable sequence variants of miRNA can include: substitutional, insertional or deletional variants. Insertions include 5' and/or 3' terminal fusions as well as intrasequence insertions of single or multiple residues. Insertions can also be introduced within the mature sequence. These, however, can be smaller insertions than those at the 5' or 3' terminus, on the order of 1 to 4 residues, 2 residues, and/or 1 residue.

Insertional sequence variants of miRNA are those in which one or more residues are introduced into a predetermined site in the target miRNA. Most commonly insertional variants are fusions of nucleic acids at the 5' or 3' terminus of the miRNA.

Deletion variants are characterized by the removal of one or more residues from the miRNA sequence. These variants ordinarily are prepared by site specific mutagenesis of nucleotides in the DNA encoding miRNA, thereby producing DNA encoding the variant, and thereafter expressing the DNA in recombinant cell culture. However, variant miRNA fragments may be conveniently prepared by in vitro synthesis. The variants typically exhibit the same qualitative biological activity as the naturally-occurring analogue, although variants also are selected in order to modify the characteristics of miRNA.

Substitutional variants are those in which at least one residue sequence has been removed and a different residue inserted in its place. While the site for introducing a sequence variation is predetermined, the mutation per se need not be predetermined. For example, in order to optimize the performance of a mutation at a given site, random mutagenesis may be conducted at the target region and the expressed miRNA variants screened for the optimal combination of desired activity. Various suitable techniques for making substitution mutations at predetermined sites in DNA having a known sequence can be used.

Nucleotide substitutions are typically of single residues; insertions usually will be on the order of about from 1 to 10 residues; and deletions will range about from 1 to 30 residues. Deletions or insertions preferably are made in adjacent pairs; i.e., a deletion of 2 residues or insertion of 2 residues. Substitutions, deletion, insertions or any combination thereof may be combined to arrive at a final construct.

Changes may be made to decrease the activity of the miRNA, and all such modifications to the nucleotide sequences encoding such miRNA are encompassed.

An "isolated nucleic acid or DNA" is generally understood to mean chemically synthesized DNA, cDNA or genomic DNA with or without the 3' and/or 5' flanking regions. DNA encoding miRNA can be obtained from other sources by, for example: a) obtaining a cDNA library from cells containing mRNA; b) conducting hybridization analysis with labeled DNA encoding miRNA or fragments thereof in order to detect clones in the cDNA library containing homologous sequences; and, c) analyzing the clones by restriction enzyme analysis and nucleic acid sequencing to identify full-length clones.

As used herein nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence similarity percentages (e.g., BLASTN using default parameters) are generally available. Software for performing BLAST analyses is publicly available through the National Center for Biotechnology Information.

The term "detecting the level of miR expression" generally refers to quantifying the amount of such miR present in a sample. Detecting expression of a miR, or any microRNA, can be achieved using any method, such as by qRT-PCR. Detecting expression of a miR includes detecting expression of either a mature form of the miR or a precursor form that is correlated with the miR expression. For example, miRNA detection methods involve sequence specific detection, such as by RT-PCR. miR-specific primers and probes can be designed using the precursor and mature miR nucleic acid sequences, and may include modifications which do not change the function of the sequences.

The terms "low miR-expression" and "high miR-expression" are relative terms that refer to the level of miR/s found in a sample. In some embodiments, low miR- and high miR-expression are determined by comparison of miR/s levels in a group of test samples and control samples. Low and high expression can then be assigned to each sample based on whether the expression of a miR in a sample is above (high) or below (low) the average or median miR expression level. For individual samples, high or low miR expression can be determined by comparison of the sample to a control or reference sample known to have high or low expression, or by comparison to a standard value. Low and high miR expression can include expression of either the precursor or mature forms of miR, or both.

In some instances, a disease reference standard or sample may be used. A reference standard may comprise miR levels indicative of a known cancer. A reference standard may be a composite of samples derived from cancer tissues. Comparison of test results with a disease reference and/or control can be used in diagnostic methods. In some embodiments, a test sample is processed at the same time as one or more disease reference samples and one or more normal, non-diseased, control samples.

The term "expression vector" generally refers to a nucleic acid construct that can be generated recombinantly or synthetically. An expression vector generally includes a series of specified nucleic acid elements that enable transcription of a particular gene in a host cell. Generally, the gene expression is placed under the control of certain regulatory elements, such as constitutive or inducible promoters.

The term "operably linked" is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is the to be "operably linked to" or "operatively linked to" or "operably associated with" the regulatory elements, meaning that the gene or coding region is controlled or influenced by the regulatory element.

The terms "agent" and "drug" generally refer to any therapeutic agents (e.g., chemotherapeutic compounds and/or molecular therapeutic compounds), antisense therapies, radiation therapies, or surgical interventions, used in the treatment of a particular disease or disorder.

The term "control" generally refers to a sample or standard used for comparison with an experimental sample, such as a sample obtained from a subject. In some embodiments, the control is a sample obtained from a healthy subject. In some embodiments, the control is cell/tissue sample obtained from the same subject. In some embodiments, the control is a historical control or standard value (i.e., a previously tested control sample or group of samples that represent baseline or normal values, such as the level in a control sample). In other embodiments, the control is a sample obtained from a healthy subject, such as a donor. Test samples and control samples can be obtained according to any method known in the art.

miR-494 Specific Inhibitors and miR-494 Antagonists

The terms "miRNA-494" and "miR-494" are used interchangeably and, unless otherwise indicated, refer to microRNA-494, including miR-494, pri-miR-494, pre-miR-494, mature miR-494, miRNA-494 seed sequence, sequences comprising a miRNA-494 seed sequence, and variants thereof.

In some embodiments, nucleic acids are used that are capable of blocking the activity of a miRNA (anti-miRNA or anti-miR). Such nucleic acids include, for example, antisense miR-494. For example, a "miR-494 antagonist" means an agent designed to interfere with or inhibit the activity of miRNA-494.

In certain embodiments, the miR-494 antagonist can be comprised of an antisense compound targeted to a miRNA. For example, the miR-494 antagonist can be comprised of a small molecule, or the like that interferes with or inhibits the activity of a miRNA.

In certain embodiments, the miR-494 antagonist can be comprised of a modified oligonucleotide having a nucleobase sequence that is complementary to the nucleobase sequence of a miRNA, or a precursor thereof.

In certain embodiments, the anti-miR is an antisense miR-494 nucleic acid comprising a total of about 5 to about 100 or more, more preferably about 10 to about 60 nucleotides, and has a sequence that is preferably complementary to at least the seed region of miR-494. In one embodiment, an anti-miRNA may comprise a total of at least about 5, to about 26, nucleotides. In some embodiments, the sequence of the anti-miRNA can comprise at least 5 nucleotides that are substantially complementary to the 5' region of a miR-494, at least 5 nucleotides that are substantially complementary to the 3' region of a miR-494, at least 4-7 nucleotides that are substantially complementary to a miR-494 seed sequence, or at least 5-12 nucleotide that are substantially complementary to the flanking regions of a miR-494 seed sequence.

In some embodiments, the anti-miR-494 comprises the complement of a sequence of the miR-494. In other embodiments an anti-miR-494 comprises the complement of the seed sequence or is able to hybridize under stringent conditions to the seed sequence. In certain embodiments, preferred molecules are those that are able to hybridize under stringent conditions to the complement of a cDNA encoding a mature miR-494.

It is to be understood that the methods described herein are not limited by the source of the miR-494 or anti-miR-494. The miR-494 can be from a human or non-human mammal, derived from any recombinant source, synthesized in vitro or by chemical synthesis. The nucleotide may be DNA or RNA and may exist in a double-stranded, single-stranded or partially double-stranded form, depending on the particular context.

miR-494 and anti-miR-494 nucleic acids may be prepared by any conventional means typically used to prepare nucleic acids in large quantity. For example, nucleic acids may be chemically synthesized using commercially available reagents and synthesizers by methods that are well-known in the art and/or using automated synthesis methods.

It is also be understood that the methods described herein are not limited to naturally occurring miR-494 sequences; rather, mutants and variants of miR-494 sequences are also within the contemplated scope. For example, nucleotide sequences that encode a mutant of a miR-494 that is a miR-494 with one or more substitutions, additions and/or deletions, and fragments of miR-494 as well as truncated versions of miR-494 maybe also be useful in the methods described herein.

It is also to be understood that, in certain embodiments, in order to increase the stability and/or optimize the delivery of the sense or antisense oligonucleotides, modified nucleotides or backbone modifications can be used. In some embodiments, a miR-494 or anti-miR-494 oligonucleotide can be modified to enhance delivery to target cells. Nucleic acid molecules encoding miR-494 and anti-miR-494 can be used in some embodiments to modulate function, activity and/or proliferation of immune cells.

In certain embodiments, the miR-494 antagonists can be single-stranded, double stranded, partially double stranded or hairpin structured oligonucleotides that include a nucleotide sequence sufficiently complementary to hybridize to a selected miR-494 or pre-miR-494 target sequence. As used herein, the term "partially double stranded" generally refers to double stranded structures that contain less nucleotides than the complementary strand. In general, partially double stranded oligonucleotides will have less than 75% double stranded structure, preferably less than 50%, and more preferably less than 25%, 20% or 15% double stranded structure.

In certain embodiments, the miRNA antagonist is sufficiently complementary to a portion of the miRNA or pre-miRNA sequence of a human miR-494. The miRNA antagonist can have a region that is at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% complementary to a portion of the miRNA or pre-miRNA sequence of a human miRNA.

Useful miRNA antagonists include oligonucleotides have at least 6, 7, 8, 9, 10, 11, 12, 13, 14, 15, 16, 17, 18, 19, 20 or more contiguous nucleotides substantially complementary to an endogenous miRNA or pre-miRNA that is overexpressed in a test subject as compared to a control subject. The disclosed miRNA antagonists preferably include a nucleotide sequence sufficiently complementary to hybridize to a miRNA target sequence of about 12 to 25 nucleotides, and in some embodiments, about 15 to 23 nucleotides. In some embodiments, there will be nucleotide mismatches in the region of complementarity. In a certain embodiment, the region of complementarily will have no more than 1, 2, 3, 4 or 5 mismatches.

In some embodiments, the miRNA antagonist is "exactly complementary" to hsa-miR-494. Thus, in one embodiment, the miRNA antagonist can anneal to the miRNA to form a hybrid made exclusively of Watson-Crick base pairs in the region of exact complementarity. Thus, in some embodiments, the miRNA antagonist specifically discriminates a single-nucleotide difference. In such cases, the miRNA antagonist only inhibits miRNA activity if exact complementarity is found in the region of the single-nucleotide difference. Also, in certain embodiments, the miRNA antagonists are oligomers or polymers of ribonucleic acid (RNA) or deoxyribonucleic acid (DNA) or modifications thereof. miRNA antagonists include oligonucleotides that contain naturally-occurring nucleobases, sugars and covalent internucleoside (backbone) linkages.

Delivery of Oligonucleotides and Expression Vectors to a Target Cell or Tissue

Expression vectors that contain anti-miR-494 coding sequence can be used to deliver an anti-miR494 to target cells. In certain embodiments, expression vectors can contain an anti-miR-494 sequence, optionally associated with a regulatory element that directs the expression of the coding sequence in a target cell. It is to be understood that the selection of particular vectors and/or expression control sequences to which the encoding sequence is operably linked generally depends (as is understood by those skilled in the art) on the particular functional properties desired; for example, the host cell to be transformed.

It is also to be understood that vectors useful with the methods described herein are preferably capable of directing replication in an appropriate host and of expression of the anti-miR-494 in a target cell, tissue or organ.

It is also to be understood that a useful vector can include a selection gene whose expression confers a detectable marker such as a drug resistance. Non-limiting examples of selection genes include those vectors that encode proteins that confer resistance to antibiotics or other toxins, e.g., ampicillin, neomycin, methotrexate, or tetracycline, complement auxotrophic deficiencies, or supply critical nutrients withheld from the media. It is also to be understood that the detectable marker can optionally be present on a separate plasmid and introduced by co-transfection.

It is also to be understood that expression control elements can be used to regulate the expression of an operably linked coding sequence. Non-limiting examples include: inducible promoters, constitutive promoters, enhancers, and other regulatory elements. In some embodiments an inducible promoter is used that is readily controlled, such as being responsive to a nutrient in the target cell's medium. It is also to be understood that other methods, vectors, and target cells suitable for adaptation to the expression of miR-494 specific inhibitors in target cells can be readily adapted to the specific circumstances.

In certain embodiments, the anti-miR-494 oligonucleotide is delivered to a target cell. In other embodiments, an expression vector encoding the anti-miR-494 is delivered to a target cell where the anti-miR-494 is expressed. It is to be understood that different methods for delivery of oligonucleotides and expression vectors to target cells can be used.

In certain embodiments, the target cells may be present in a host, such as in a mammal, or may be in culture outside of a host. Thus, the delivery of miR-494 or anti-miR-494 to target cells in vivo, ex vivo and in vitro can accomplished in a suitable manner. In certain embodiments, a miR-494 or anti-miR-494 oligonucleotide is delivered to a target organ or tissue.

In certain embodiments, the mutation of a cell can be modulated (e.g., suppressed) by administering an anti-miR-494 oligonucleotide to the cells. The numbers and/or activity of the cells can be modulated by administering an anti-miR-494 oligonucleotide to the cancer cells or to pre-cancerous cells. In certain embodiments, the immune function and/or development of the cells can be modulated by delivering the anti-miR-494 to the cells.

It is to be understood that the delivery of oligonucleotides and/or expression vectors to a target cell can be accomplished using different methods. In certain embodiments, a transfection agent can be used. In general, a transfection agent (e.g., a transfection reagent and/or delivery vehicle) can be a compound or compounds that bind(s) to or complex(es) with oligonucleotides and polynucleotides, and enhances their entry into cells. Non-limiting examples of useful transfection reagents include: cationic liposomes and lipids, polyamines, calcium phosphate precipitates, polycations, histone proteins, polyethylenimine, polylysine, and polyampholyte complexes.

Another delivery method can include electroporating miRNA/s into a cell without inducing significant cell death. In addition, miRNAs can be transfected at different concentrations.

Non-limiting examples of useful reagents for delivery of miRNA, anti-miRNA and expression vectors include: protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups can include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers).

In certain embodiments, anti-miR-494 nucleic acids and a transfection reagent can be delivered systematically such as by injection. In other embodiments, they may be injected into particular areas comprising target cells, such as particular organs, for example a solid cancer tissue. The skilled artisan will be able to select and use an appropriate system for delivering anti-miRNA-494 or an expression vector to target cells in vivo, ex vivo and/or in vitro without undue experimentation.

Regulation and Modulation of MicroRNAs

MicroRNAs (miRNAs) have an important role in the development of chemosensitivity or chemoresistance in different types of cancer. Activation of the ERK1/2 pathway is a major determinant of diverse cellular processes and cancer development and is responsible for the transcription of several important miRNAs. Described herein is a link between the ERK1/2 pathway and BIM expression through miR-494. BIM (also called BCL2-like 11) is one of the most important apoptosis regulators. BIM is involved in drug resistance in non-small-cell lung cancer (NSCLC). BIM expression levels are regulated also by miRNAs, leading to chemoresistance in NSCLC. Moreover, MEK-ERK signaling negatively regulated BIM expression.

Described herein is the analysis of microRNA expression profile in 293A PED$^{S104G}$ over-expressing cells compared with PED$^{WT}$ 293A cells. This mutated PED cannot be phosphorylated in Ser$^{104}$, so PED$^{S104G}$ binds and retains ERK1/2 in the cytosol, suppressing its transcriptional effects.

The blockade leading to accumulation of the ERKs in the cytoplasm confers a particular microRNA signature on affected cells, with miR-494 among the most down-regulated miRNAs. Moreover, BIM is a bona fide target of miR-494; and, BIM down-regulation by miR-494 induces TNF-related apoptosis-inducing ligand (TRAIL) resistance in NSCLC cells.

ERK1/2 nuclear activity was blocked through the over-expression of an ERK1/2 natural interactor, the protein PED/PEA-15. A microRNA expression profile was performed. miR-494 was the most down-regulated microRNA after ERK1/2 inactivation. Moreover, miR-494 induced TRAIL resistance in non-small-cell lung cancer (NSCLC) through the down-modulation of BIM. Elucidation of this ERK1/2 pathway that regulates apoptosis and cell proliferation through miR-494 in NSCLC illustrates mechanisms responsible for TRAIL resistance and provides an additional anticancer therapeutics.

ERK1/2 pathway controls several cellular functions, such as proliferation, survival, and migration. When dysregulated, this cascade plays a major role in various pathological conditions, particularly cancer. ERK1/2 is regulated in part by its sub-cellular localization. ERK localization within the cell may be controlled by phosphoprotein enriched in diabetes (PED, also known as PEA-15 [phosphoprotein enriched in astrocytes]), a small, death effector domain-containing protein. PEA-15 has at least two distinct functions within the cell: it regulates ERK1/2 localization by sequestering the ERKs in the cytoplasm, and it blocks apoptosis by interfering with the assembly of the death-induced signaling complex. PED function is regulated by phosphorylation on two different serine residues: Ser104, phosphorylated by protein kinase C; and, Ser116, phosphorylated by AKT/protein kinase B and CamKII (calcium calmodulin kinase II). Phosphorylation of PED by protein kinase C substantially reduces ERK binding, whereas phosphorylation by CamKII has no effect on ERK binding. PED modifies ERK signaling by excluding ERK from the nucleus. The Raf/MAPK/ERK cascade is now believed to have a regulatory role in microRNA expression.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

miR-494 is Regulated by PED Through ERKJ/2.

To block ERK1/2 transcriptional activity, myc-PED$^{S104G}$ cDNA was over-expressed into 293A cells that exhibit low endogenous PED levels. As control, PED$^{wt}$ cDNA-over-expressing cells were used (FIG. 1A).

In PED$^{S104G}$ mutant, the Ser at position 104 was changed in Gly (PED$^{S104G}$) so PED$^{S104G}$ could not be phosphorylated in Ser104 and it bound and retained ERK1/2 in cytosol. A nucleo/cytosol separation was then performed.

Figure 1B:
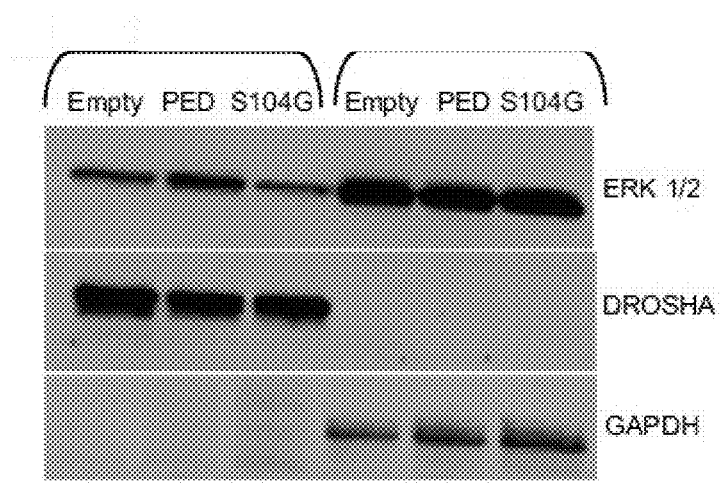
Figures 1C, 1D:
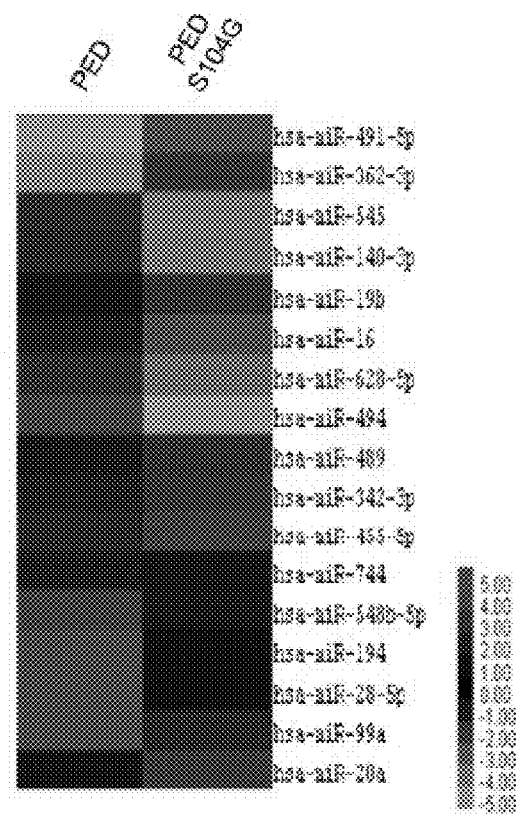

As shown in FIG. 1B, PED$^{S104G}$ reduced nuclear ERKs level compared with PED$^{WT}$. The global miRNA expression profiles (FIG. 1C) were examined by TaqMan Array Cards. MicroRNAs with a fold-change<−3.00 are shown (FIG. 1D). miR-494 the most down-regulated microRNA in PED$^{S104G}$ cells.

miR-494 Promoter Analysis.

To analyze the role of ERK1/2 on miR-494 expression, the expression levels of primary (pri)-miR-494 and premiR-494 were evaluated by quantitative (q)RT-PCR analysis in PED$^{wt}$- and PED$^{S104G}$-transfected 293A cells.

As shown in FIGS. 2A and 2B, PED$^{S104G}$ over-expression induced a strong down-regulation of both pri-miRNA-494 and pre-miR-494 levels.

Figure 2E:
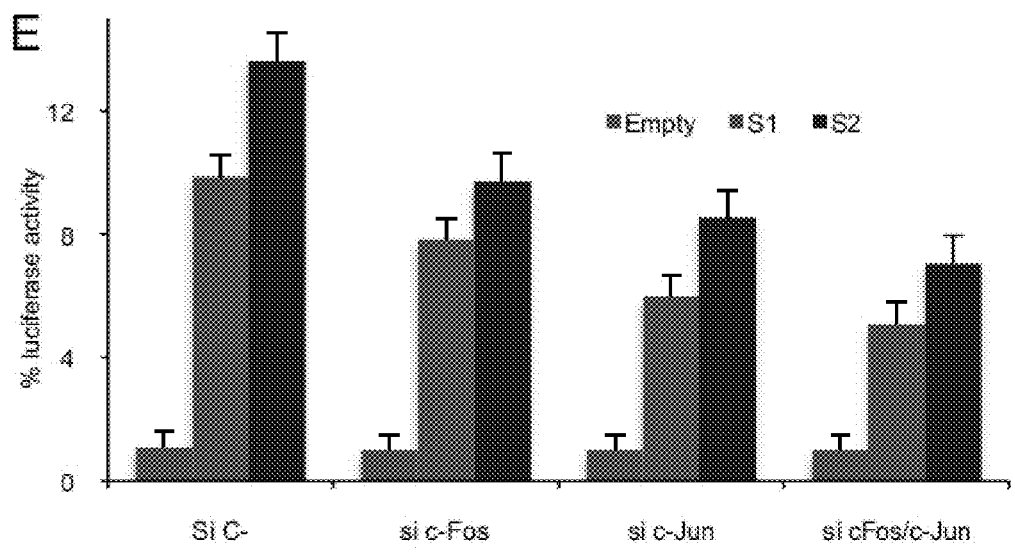
Figure 2F:
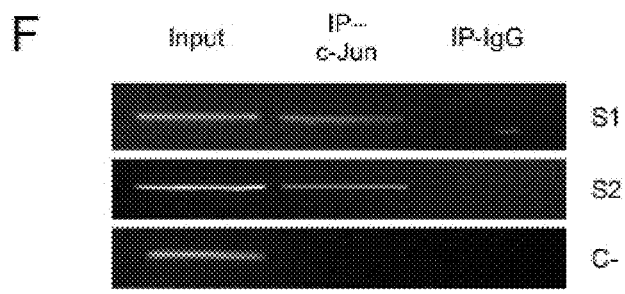
Figure 2G:
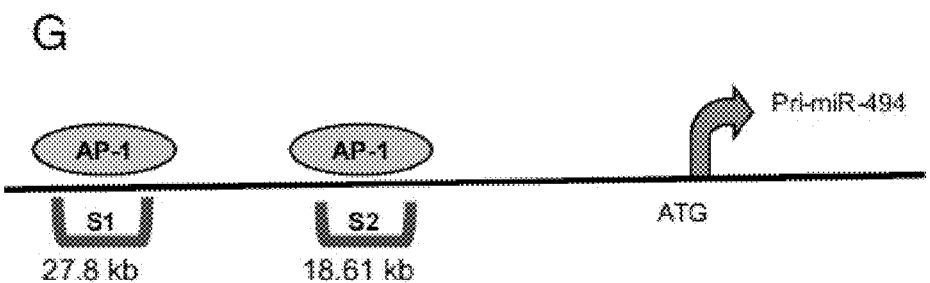

To confirm the direct involvement of ERK1/2 on miR-494 expression levels, the upstream sequence of miR-494 was analyzed with the Promoter.2 prediction server. Two regions that could be transcriptional promoters were located ~27.8 kb and 18.61 kb upstream of the 5' end of pri-miR-494 (FIG. 2G).

To confirm this upstream region is a miR-494 transcriptional promoter, reporter plasmids were constructed by inserting fragments of about 400 bp (S1=422 bp, S2=425 bp) into the promoter-less vector pGL3basic. The luciferase assay showed that both sequences increased luciferase activity compared with the empty vector (FIG. 2C) showing that both regions could be can promoter a miR-494.

To confirm that the S1 and S2 promoter sequences were regulated by ERK1/2, it was determined whether the interference of ERK1/2 could lower the luciferase activity after S1 and S2 over-expression. As shown in FIG. 2D, the silencing of ERK1/2 induced a down-regulation of the luciferase activity of both pGL3b-S1 and pGL3b-S2. It was found that the AP1 transcription factor was predicted to bind the sequence S1 and S2 upstream miR-494 gene and to activate miR-494 expression.

ERK1/2 phosphorylates and activates the c-Jun and c-Fos protooncoproteins, which participate in the formation of the AP1 transcription factor as homodimer or heterodimer. The c-Fos and c-Jun silencing was able to reduce the luciferase activity on S1 and S2 over-expression, demonstrating that S1 and S2 sequences were regulated by AP1 (FIG. 2E).

The down-regulation of ERK1/2, c-Jun, and c-Fos by siRNA through Western blot (FIG. 7A). To verify a direct binding of c-Jun on miR-494 promoter, out chromatin immunoprecipitation (ChIP) assays were carried out. Three chromatin regions were analyzed: two spanning the AP-1 binding site S1 and S2 and one as a negative control, a region ~31 kb upstream of the premiR-494 5' end, where there was no predicted binding site for AP-1 found. The ChIP assay of c-Jun showed remarkable AP-1 binding at ChIP analyzed regions S1 and S2 proximal to the promoter (FIG. 2F). No chromatin enrichment by c-Jun ChIP was observed in negative control, verifying the specificity of the ChIP assay. These results confirm that S1 and S2 are promoting sequences that are regulated by ERK1/2 through AP1.

miR-494 Directly Targets BIM 3' UTR.

Figure 3A:
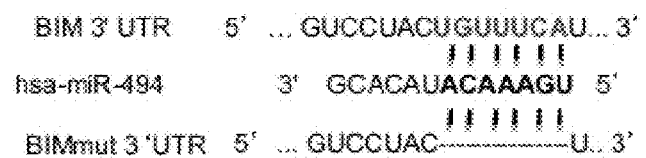
FIGS. 3A-3D. BIM is target of miR-494.

A bioinformatics search (Targetscan, Pictar, RNhybrid) was performed for putative mRNA targets of miR-494. Among the candidate targets, the 3' UTR of human BIM (nucleotides 2829-2835, NM_001204106) was selected, which contained a region that matched the seed sequences of hsa-miR-494 (FIG. 3A). To verify whether BIM is a direct target of miR-494, BIM 3' UTR containing miR-494 binding site was cloned into the pGL3 control vector downstream the luciferase ORF. This reporter construct was used to transfect Meg01 cells, which express very low levels of miR-494 compared with 293A cells (FIG. 7B) and are highly transfectable. Increased expression of this miRNA on transfection was confirmed by qRT-PCR (FIG. 7C). A significant reduction of luciferase activity was found in samples cotransfected with a plasmid harboring the 3' UTR of BIM mRNA and miR494 compared with the cells transfected with a scrambled miR of the same length (FIG. 3B, Left).

Figure 3B:
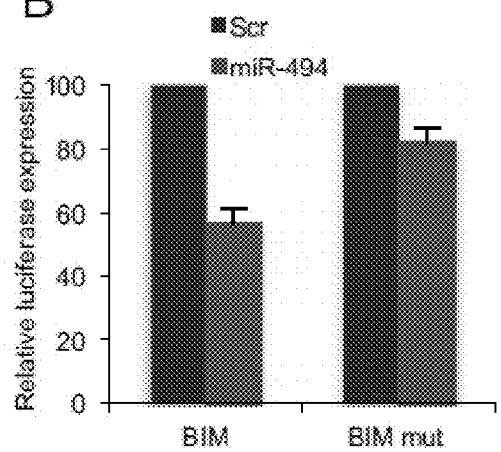

Conversely, when luciferase assays were performed by using a plasmid harboring the 3' UTR of BIM mRNA, where the binding site for miR-494 was deleted by site-directed mutagenesis, a consistent reduction of the miR-494 inhibitory effect on BIM 3' UTR was observed (FIG. 3B, Right).

Figure 3C:
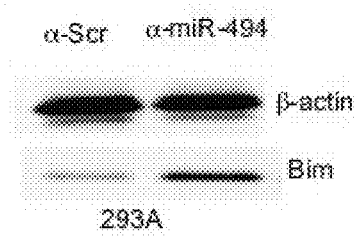
Figure 3D:
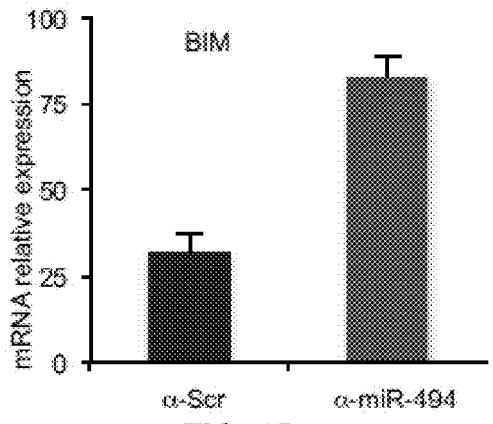

To confirm that miR-494 could affect BIM expression in cell lines, regulated miR-494 was down-regulated in 293A cells by anti-miR-494 transfection. Decreased expression of this miRNA on transfection was confirmed by qRT-PCR (FIG. 7D).

miR-494 down-regulation significantly increased the endogenous levels of BIM either at protein or mRNA levels compared with 293A cells transfected with the scrambled miR (FIGS. 3C and 3D). Taken together, these results show that BIM 3' UTR is a direct target of miR-494.

BIM is Regulated by PED-ERK1/2 Through AP1.

$PED^{wt}$ or $PED^{S10G}$ was transfected into 293A cells and then BIM expression levels were evaluated to investigate BIM expression regulation by PED-ERK1/2-miR494.

Figure 4A:
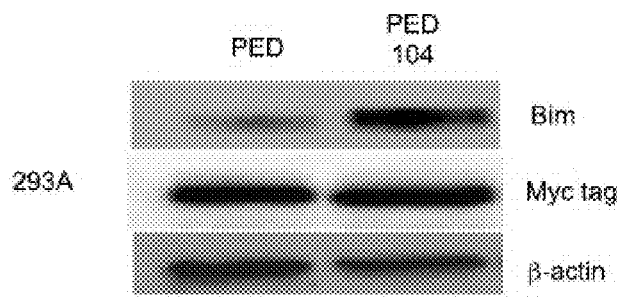
FIGS. 4A-4E. BIM expression is regulated by PED through ERK1/2.
Figure 4B:
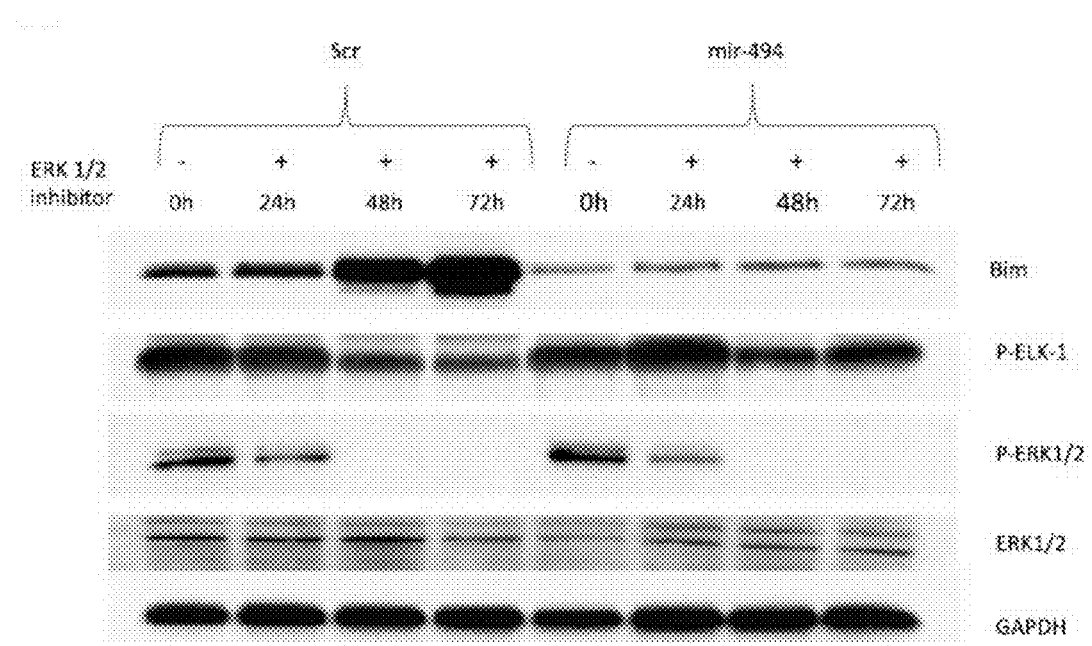

A marked increase in BIM expression on PED transfection compared with $PED^{wt}$ was observed (FIG. 4A). To confirm that the effect of PED on BIM expression was mediated by ERK1/2, miR-494-transfected cells were treated with ERK inhibitor II (FR180204) at different time points and then analyzed BIM expression levels by Western blot. The ERK inhibitor II was able to reduce cellular levels of p-ERK 1/2 and p-Elk1, an ERK 1/2 nuclear substrate (FIG. 4B).

Moreover BIM expression was strongly up-regulated after 48 h and 72 h of ERK1/2 inhibitor. This effect was not present in cells transfected with miR-494 (FIG. 4B); thus, the over-expression of miR-494 was able to rescue PED effects on BIM expression.

Figure 4C:
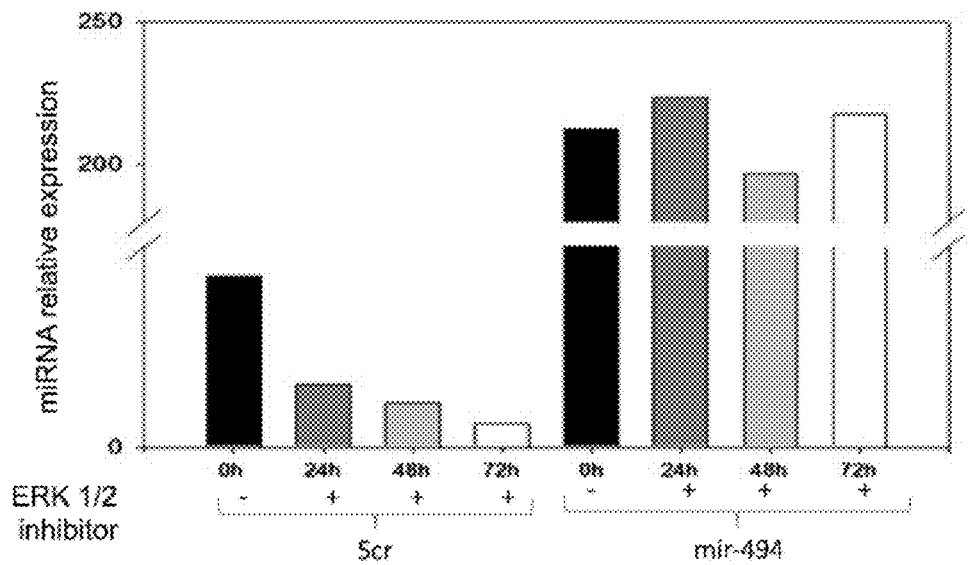
Figures 4D, 4E:
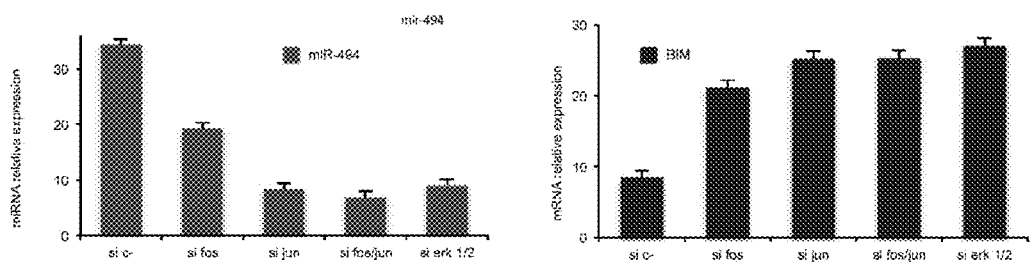

Also, as shown in FIG. 4C, Left, miR-494 is down-regulated after 48 h and 72 h of ERK1/2 inhibitor corroborating ERK 1/2 role in miR-494 expression. To confirm that BIM up-regulation was related to the down-regulation of ERK1/2 and consequently to the down-modulation of AP1 (c-Fos/c-Jun), BIM mRNA and miR-494 expression after ERK1/2 and AP1 (c-Junk-Fos) silencing in 293A cells using qRT-PCR were analyzed (FIGS. 4D and 4E). It was observed that a miR-494 down-regulation and BIM mRNA up-regulation after silencing of c-Jun, c-Fos, ERK1/2, and c-Junk-Fos together. These results strongly show that BIM is regulated by PED-ERK1/2 through AP1.

Role of miR-494 and BIM in NSCLC.

Figure 8F:
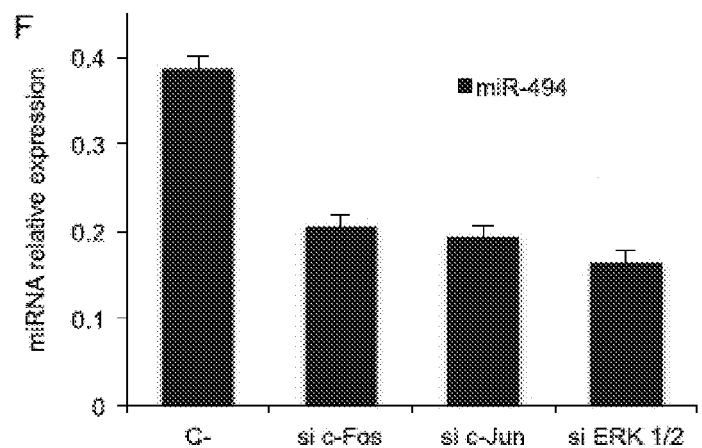
FIG. 8F: qRT-PCR in A549 cells showing miR-494 down-regulation after ERK1/2 siRNA.

To confirm the functional role of the axis PED-ERK-miR-494-BIM in tumorigenesis, the endogenous levels of miR-494 and BIM were evaluated in a panel of five NSCLC cells. As assessed by qRT-PCR, an inverse correlation was found between miR-494 expression and BIM mRNA expression in most NSCLC cell lines analyzed (FIGS. 8A-8C).

These results show that high expression levels of miR-494 is one of the mechanisms acting to negatively regulate BIM in NSCLC. To confirm that miR-494 affects endogenous levels of BIM in lung cancer, the effects of the ectopic expression of miR-494 in the H460 lung carcinoma cell line, which expresses low levels of miR-494, were analyzed.

Figures 5A, 5B:
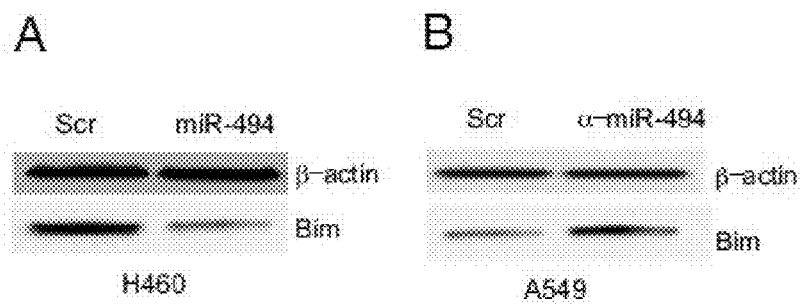
FIGS. 5A-5G. miRNA-494 inhibits apoptosis in NSCLC through BIM down-regulation.

As shown in FIG. 5A, BIM protein was clearly reduced in H460 cells on miR-494 over-expression. Conversely, knockdown of miR-494 by anti-miR-494 in A549 lung adenocarcinoma cells, which expresses high levels of endogenous miR-494, increased the protein level of BIM (FIG. 5B).

Figure 5C:
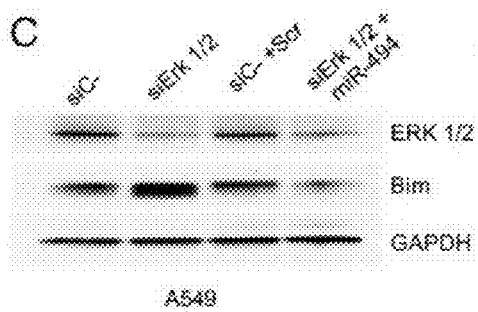

To confirm whether this regulation also might occur through PED-ERK1/2 pathway in NSCLC cells, ERK1/2 was silenced in A549 cells. The ERK 1/2 silencing was able to decrease miR-494 expression in A549 cells (FIG. 8D, Left) and to induce BIM up-regulation (FIG. 5C and FIG. 8E, Left), as assessed by WB and qRT-PCR. On the contrary, miR-494 transfection antagonized the siERK1/2 effect (FIG. 5C and FIGS. 8D and 8E, Right). To confirm the role of AP1 on miR-494 transcriptional activation and BIM up-regulation in NSCLC, A549 cells were transfected with siRNAs targeting ERK1/2, c-Fos, and c-Jun (FIG. 5D).

Figure 5D:
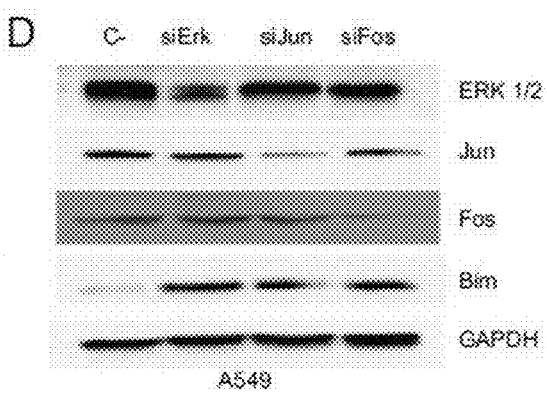

The silencing of ERK1/2, c-Fos, and c-Jun induced miR-494 down-regulation (FIG. 8F) and BIM up-regulation (FIG. 5D). These results show that BIM regulation by PED-ERK1/2 through AP1 is a relevant pathway in NSCLC.

miRNA-494 Inhibits Apoptosis in NSCLC Through BIM Down-Regulation.

Figure 5E:
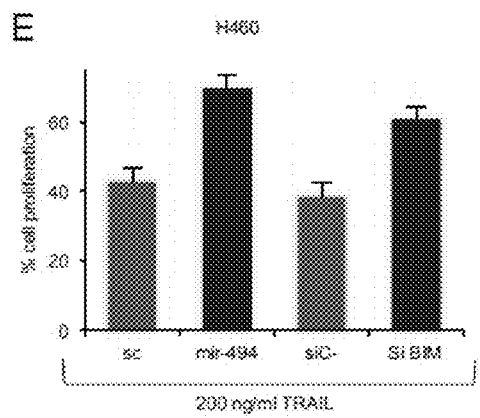
Figure 5F:
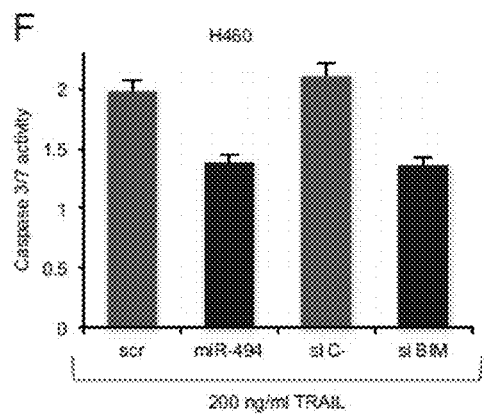

Because BIM silencing is involved in the resistance to different drugs, the role of BIM down-regulation through miR-494 in TRAIL resistance was evaluated. To test whether miR-494 over-expression in TRAIL-sensitive H460 cells could induce TRAIL resistance, a proliferation and apoptosis assay in H460 cells was performed. The H460 cells were transfected with either scrambled miRNA or miR-494 and with either a control siRNA or BIM siRNA. After 48 h, transfected cells were exposed to TRAIL for 16 h. Cell proliferation was assessed using a 3-(4,5-dimethyl-thiazol-2-yl)-2,5-diphenyltetrazolium bromide assay, and apoptosis was assessed by measuring caspase 3/7 activity. The H460 cells, after miR-494 enforced expression or BIM down-regulation, showed a very high proliferation rate and were more resistant to TRAIL-induced cell death (FIGS. 5E and 5F).

Figure 8G:
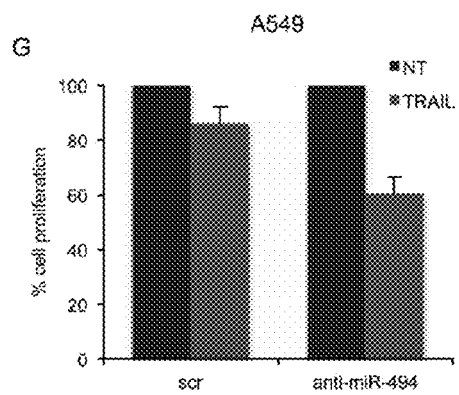
FIG. 8G and FIG. 8H: Proliferation and Caspase 3-7 assay on A549 cells after miR-494 transfection and TRAIL treatment. Significance values of P<0.05 relative to untreated A549 cells.
Figure 8H:
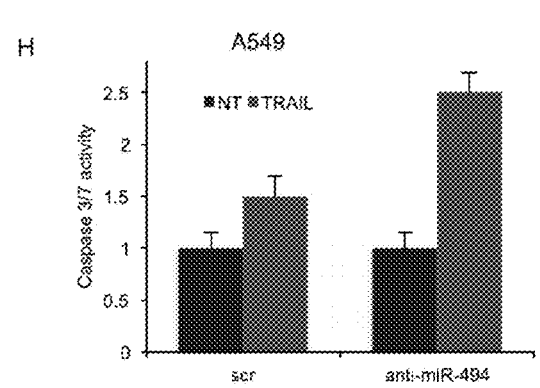
Figure 8I:
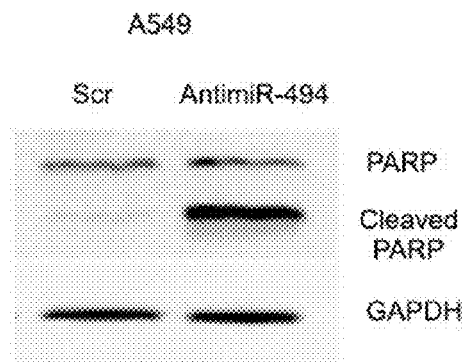
FIG. 8I: Western blot performed on A459 cells transfected with scrambled, miR-494 and treated with (400 ng/mL) TRAIL for 40 min Data are presented as ±SD.

To further confirm the role of miR-494 in NSCLC, a proliferation and caspase 3/7 assay were also performed in TRAIL-resistant A549 cells. The A549 cells showed lower proliferation rate after TRAIL treatment and readily underwent TRAIL-induced cell death (FIGS. 8G and 8H).

Figure 5G:
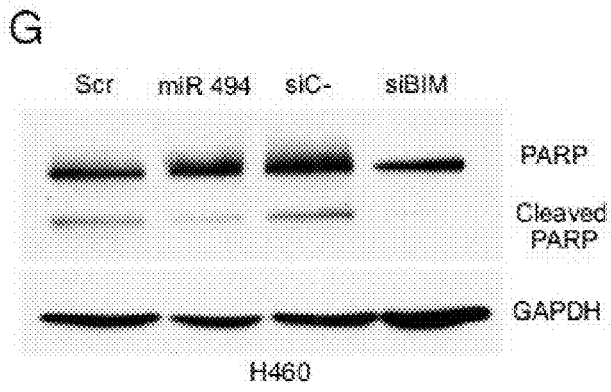

To determine whether deregulation of miR-494 or BIM could change the response to TRAIL, sensitive H460 cells or resistant A549 cells were exposed to TRAIL for 40 min, and poly (ADP ribose) polymerase activation was assessed by Western blot. Over-expression of miR-494 or BIM silencing in TRAIL-sensitive H460 cells led to a reduction in PARP cleavage (FIG. 5G); conversely, down-regulation of miR-494 in the resistant A549 line led to an increase of in PARP cleavage (FIG. 8). These results further show that miR-494-mediated BIM down-regulation plays an important role in TRAIL resistance in NSCLC.

Figure 9A:
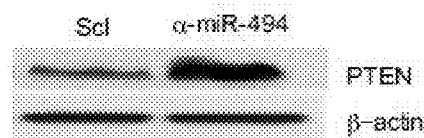
FIG. 9A: Western blot showing PTEN expression after anti-mir-494 transfection in A549 cells.

Effects of miR-494 on Tumorigenicity In Vivo.

miR-494 has an important role in tumor progression in myeloid-derived suppressor cells by targeting phosphatase and tensin homolog (PTEN). In confirming whether miR-494 has a role in tumorigenicity of NSCLC, it was determined that there is a strong up-regulation of PTEN after transfection of anti-miR-494 in A549 (FIG. 9A), confirming that PTEN is also a miR-494 target in NSCLC.

Figure 9B:
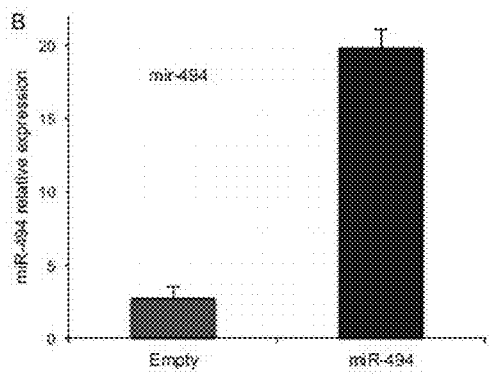
FIG. 9B: qRT-PCR showing miR-494 expression in H460 cells stably infected with empty vector or miR-494.
Figure 9C:
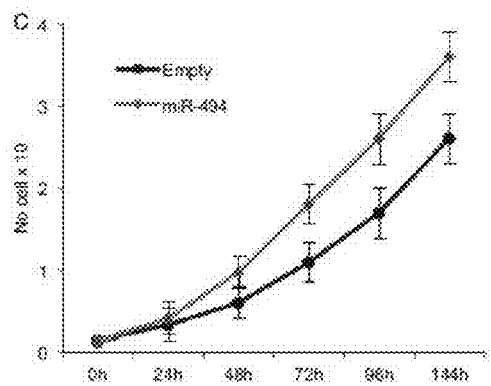
FIG. 9C: Growth curve analyses on H460 cells infected with control or miR-494 lentiviruses.
Figure 10A:
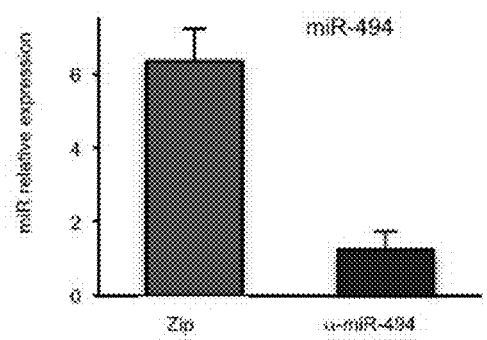
FIG. 10A: qRT-PCR showing miR-494 expression in A549 cells stably infected with empty vector (ZIP) or a-miR-494.
Figure 10B:
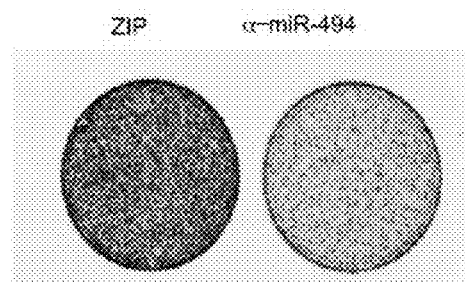
FIG. 10B and FIG. 10C: Clonogenic assays on A549 cells infected with control (ZIP) or α-miR-494 lentiviruses. The clonogenic assays were performed three times. Representative plates are shown. Columns mean number of clones derived from 500 cells plated.
Figure 10C:
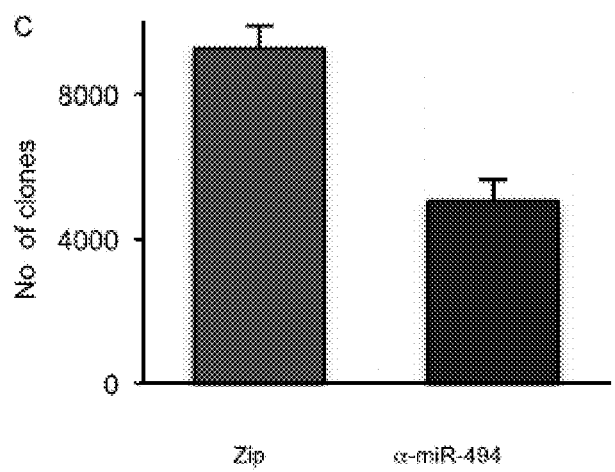
Figure 10D:
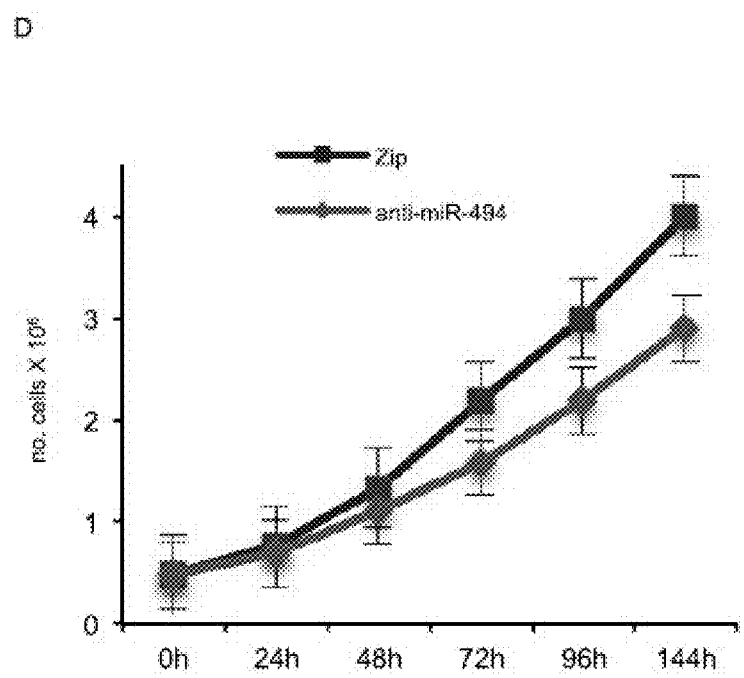
FIG. 10D: Growth curve analyses on A549 cells stably infected with empty vector (ZIP) or a-miR-494 lentiviruses.

To analyze tumorigenicity of miR-494 in vivo, H460 cells were stably infected with a GFP lentivirus construct that was either empty or contained full-length miR-494 and A549 cells with a GFP lentivirus construct that was either empty (ZIP) or contained anti-miR-494. The upregulation and down-regulation of miR-494 was confirmed by qRT-PCR (FIGS. 9B and 10A).

The influence of miR-494 on cell proliferation was determined by generating growth curves and performing clonogenic assays using H460- and A549-stably infected cell lines.

As shown in FIGS. 6A and 6B, FIG. 9C and FIGS. 10B-10D, the miR-494 overexpression significantly increased H460 cell proliferation, whereas its down-regulation in A549 decreased cell proliferation.

Figure 6C:
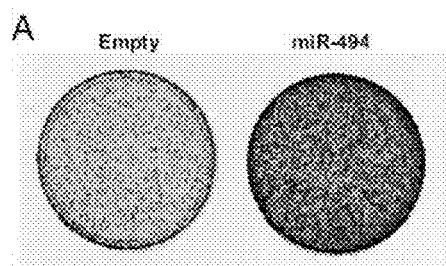
Figure 6C:
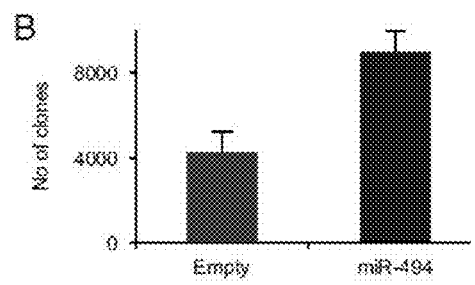
Figure 6C:
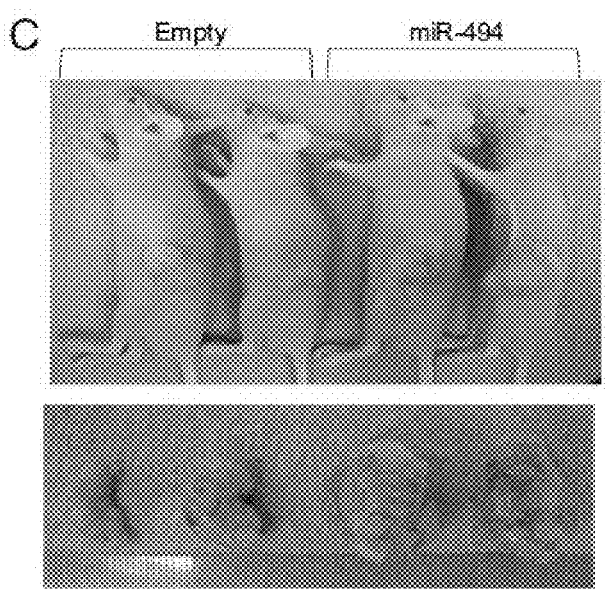
Figure 6D:
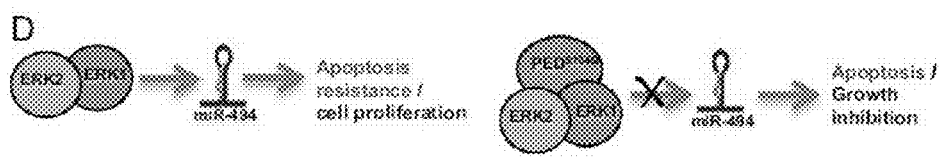
Figure 9D:
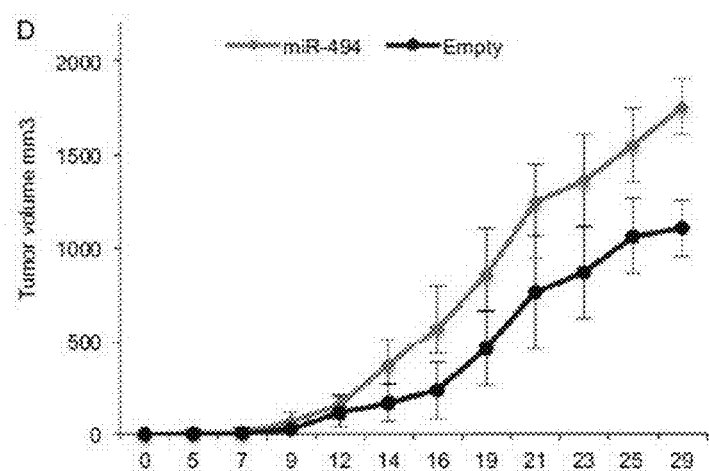
FIG. 9D: Growth curve of engrafted tumors in nude mice injected with H460 cells stably infected with empty vector or miR-494.

Then, H460-miR-494 cells were injected into the subcutis of the flank of five nude mice (FIG. 6C). Thirty days after injection, over-expression of miR-494 resulted in a significant increase of tumor growth compared with the tumors expressing empty vector (FIG. 6C and FIG. 9D).

Figure 9E:
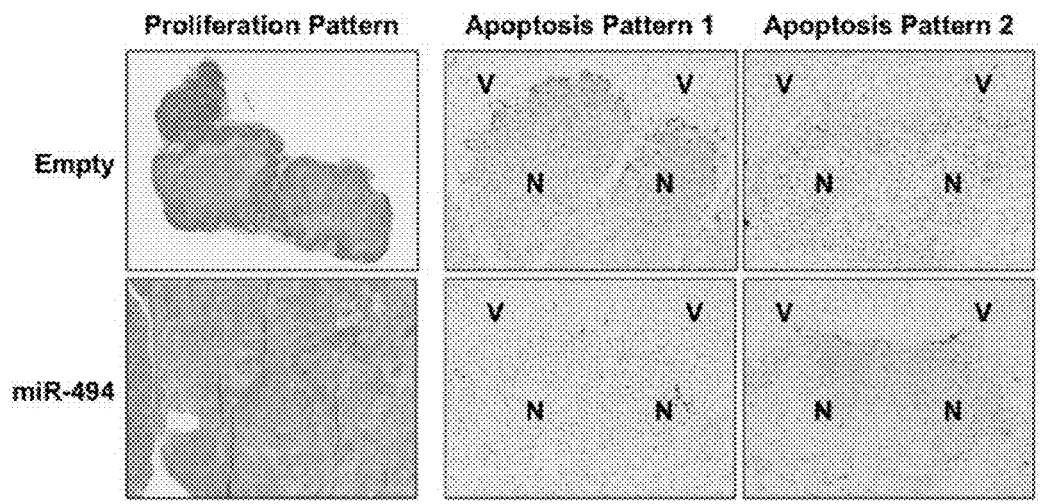
FIG. 9E: Immunohistochemistry was performed on engrafted tumor samples derived from H460 cells infected with control or miR-494 lentiviruses. Relative to masses derived from empty vectors (top left), cells over-expressing miR-494 (bottom left) formed much larger masses. Control and miR-494-expressing specimens could not be separated based on the degree of either cell proliferation (left column, original magnification=10×) or apoptosis (middle and right columns, original magnification=200×) at the interface between viable xenograft (V) and necrotic regions (N). Immunohistochemical stains: proliferation=anti-Ki67, apoptosis=anti-caspase-3, both using diaminobenzidine as the chromogen to yield a brown product on a pale blue (hematoxylin) background.
Figure 10E:
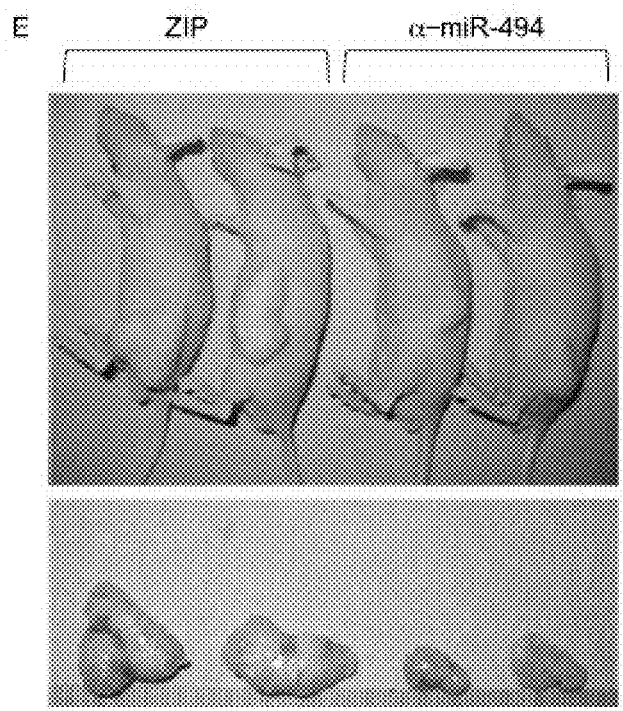
FIG. 10E: Comparison of tumor engraftment sizes in nude mice injected with A549 cells stable infected with ZIP vector or a-miR-494.
Figure 10F:
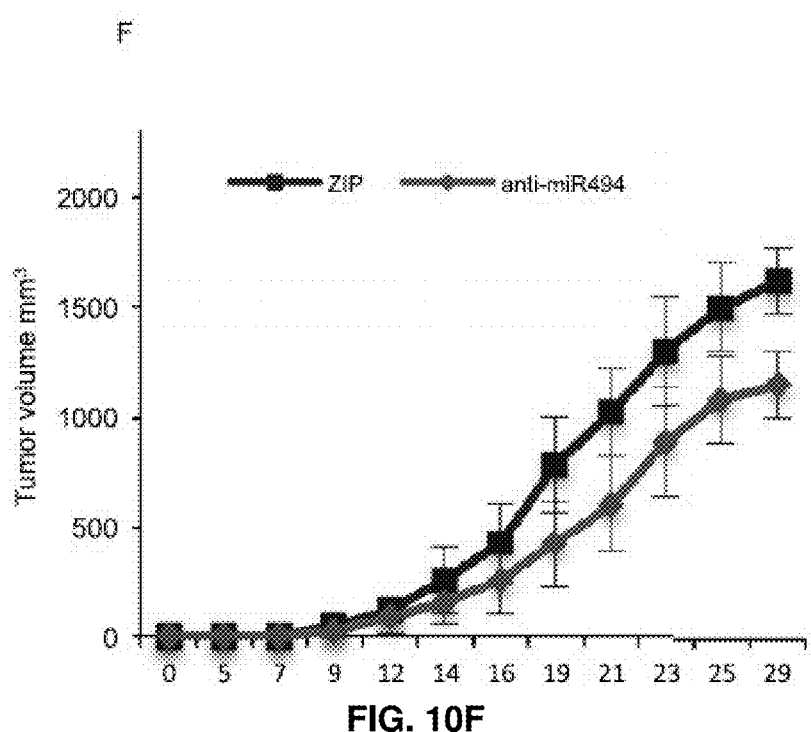
FIG. 10F: Growth curve of engrafted tumors in nude mice injected with A549 cells stably infected with empty vector (ZIP) or a-miR-494 lentiviruses.

To further confirm the miR-494 effect on tumorigenicity A549-anti-miR-494, cells also were injected into the flank of five nude mice (FIGS. 10E and 10F). In this case, down-regulation of miR-494 resulted in a significant decrease of tumor growth compared with the tumors expressing empty vector (ZIP). Histopathological analysis indicated that the masses comprising cells over-expressing miR-494 were much larger than those transfected with an empty vector; apoptotic cells at the interface between the necrotic cores and viable tissue were fewer in number and seldom occurred together in masses produced by miR-494-transfected cells, whereas they were commonly clustered at this site in control masses (FIG. 9E). These in vivo data further confirm the in vitro data and further show the importance of miR-494 as a regulatory factor in the progression of lung cancer.

Discussion of Examples

Described herein is an approach is based on the use of a mutant of PED, a protein able to block ERK1/2 in the cytoplasm, thus blocking only the ERK1/2 nuclear pathway and not the cytoplasmic one. In this way, the induction of transcription factors activated by ERK was blocked and the miRNAs regulated by ERK1/2 were evaluated. Several miRNAs down-regulated after the $PED^{S104G}$ over-expression were found; miR494 exhibited the highest fold change.

There is a direct connection of $PED^{S104}$ over-expression and down-regulation of miR-494. Particularly, there is a down-regulation in both the mature form and pri-miRNA, thus showing a direct link between the PED mutant over-expression and miR-494 transcriptional regulation.

Moreover, AP1 (c-Jun and c-Fos) directly binds to the miR-494 promoter. Indeed, the silencing of AP1 and ERK1/2 led to a decrease of two transcriptional promoter sites activity, thus showing a significant role of AP1 in the transcription of miR-494.

To analyze the functional role of miR-494, protein targets were investigated, such as the target genes involved in intracellular signaling (and cell death), e.g., the one encoding BIM (BIM is a protein that promotes apoptosis of many tumor cells, such as, for example, lung cancer, breast cancer, osteosarcoma, and melanoma).

Described herein is not only an inverse correlation between the expression of miR-494 and BIM in 293A cells, but also that miR-494 directly targets BIM 3' UTR. The over-expression of $PED^{S104G}$ led to an up-regulation of BIM expression and this up-regulation was mediated by miR-494 down-regulation through ERK1/2 inhibition.

Also, miR-494 down-regulation and BIM up-regulation was mediated by AP1.

ERK1/2, by activating miR-494, which in turn targets BIM 3' UTR, induces the down-regulation of BIM, thus shown is an inverse relation between miR-494 and BIM expression.

Also described herein is the role of miR-494 in TRAIL resistance (TRAIL is an apoptosis-based antitumor agent). The over-expression of miR-494 in H460 TRAIL-sensitive cells, by down-regulating BIM, increased the resistance to TRAIL induced apoptosis. The same result was obtained on TRAIL-resistant A549 cells, the down-regulation of miR494 made A549 cells more sensitive to TRAIL-induced apoptosis; thus confirming the relevant role of miR-494 in TRAIL resistance.

Also described herein is the role miR-494 has in NSCLC tumorigenicity. The miR-494 role in tumorigenesis was analyzed in vivo by injecting H460 cells stably infected with full-length miR-494 lentivirus and A549 cells stably infected with a-miR-494 into nude mice. There was an increase of tumor burden in miR-494-over-expressing tumors and a decrease of tumor burden in mice injected a-miR-494.

Also described herein is a pathway showing the involvement of ERK1/2 in the regulation of the apoptotic process and cell proliferation. There is a link between ERK 1/2 pathway and BIM expression through miR-494. In addition, miR-494 has a pivotal role in TRAIL resistance in NSCLC. The down-regulation of miR-494 is also useful in determining drug sensitivity and inhibition of proliferation; in particular, in the development of specific therapeutic strategies for lung cancer.

Materials and Methods

Cell Culture, Transfection, and Chemicals.

H460, A549, 293A and Meg-01 cells were seeded and grown in RPMI with 10% FBS, L-glutamine, and antibiotics (Invitrogen). All of the transfections were performed by using Lipofectamine 2000 (Invitrogen), as suggested by the manufacturer. The 293A cells were transfected with $PED^{wt}$ and $PED^{S104G}$ expression plasmid. All cell lines used were cultured to 80% confluence in p60 plates with a serum-free medium without antibiotics and then transfected with 100 nmol of pre-miR-494 oligonucleotides or negative control or anti-miR-494 for 48 h or 72 h (Ambion).

pGL3 control BIM-3' UTR, pGL3 control BIM3' UTR mutated, and pGL3 basic S1 and pGL3 basic S2 were transfected as described in the Luciferase Assay section. Super-Killer TRAIL (Alexis Biochemicals) was used. Proliferation and Caspase 3/7 assay on H460 cells after miR-494 or BIM siRNA and TRAIL treatment (200 ng/mL). Significance values of $P<0.05$ relative to untreated H460 cells. Western blot showing poly (ADP-ribose) polymerase (PARP) and PARP cleaved expression after miR-scrambled, miR-494, siRNA control (Ctr), and siBIM in H460 cells treated with (200 ng/mL) TRAIL for 40 min siRNA-c-Fos, siRNA c-Jun, siRNA ERK1/2, and siRNA were used as negative control (all Santa Cruz Biotechnology) to transfected 293A and A549 cell lines. The cells were cultured to 80% confluence and transiently transfected using Lipofectamine 2000 (Invitrogen) as described in the manufacturer's protocol.

Target Analysis.

Bioinformatics analysis was performed by using these specific programs: Targetscan, Pictar, and RNhybrid.

RNA Extraction.

Total RNA was extracted with TRIzol solution (Invitrogen), and the integrity of RNA was assessed with Agilent BioAnalyzer 2100.

Statistical Analysis.

Continuous variables are expressed as mean values±SD. The Student t test was used to determine the role of miRNA miR-494-induced TRAIL sensitivity in NSCLC expression on NSCLC cells in certain experiments.

TaqMan Array Cards.

miRNA expression profiling was performed using TaqMan Array Human miRNA Cards (cards A and B, v2.1 and v3.0, respectively; Applied Biosystems) on a 7900HT thermocycler (Applied Biosystems). These two cards are designed with 750 unique assays of human miRNAs from the Sanger miRbase v14, three endogenous control, and one negative control. miRNAs were amplified after specific RT and preamplification using Megaplex Assay Performance (Megaplex RT Primer Pools and Megaplex PreAmp pools, both from Applied Biosystems) according to the manufacturer's instructions. Expression data were normalized to the expression of the included control miRNAs.

Western Blot Analysis.

A549, 293A, and H460 cells were seeded and grown in RPMI with 10% FBS in six-well plates for 72 h. After transfection, cells were washed with cold PBS and subjected to lysis in a lysis buffer (50 mM Tris-HCl, 1 mM EDTA, 20 g/L SDS, 5 mM DTT, 10 mM phenylmethylsulfonyl fluoride). Equal amounts of protein lysates (50 μg each) and molecular weight marker (Bio-Rad Laboratories) were separated by 4% to 20% SDS-PAGE and then electrotransferred to nitrocellulose membranes. The membranes were blocked with a buffer containing 5% nonfat dry milk in Tris-buffered saline with 0.1% Tween-20 for 2 h and incubated overnight with antibodies at 4° C. After a second wash with Tris-buffered saline with 0.1% Tween 20, the membranes were incubated with peroxidase-conjugated secondary antibodies (GE Healthcare, Amersham) and developed with an enhanced chemiluminescence detection kit (Pierce).

Antibody Used for Western Blot Analysis.

β-Actin (Sigma) and GAPDH (Cell Signaling Technologies) were used as a loading control. ERK1/2 was from Promega; Myc-tag, Jun, Fos, and PTEN were from Santa Cruz Biotechnology; Caspase-3, phosphorylated ERK1/2, BIM, p-ELK1, poly (ADP ribose) polymerase antibodies were from Cell Signaling Technologies; DROSHA was from a beam; and Ki67 was from Thermo Scientific.

Real-Time PCR.

qRT real-time PCR was performed using a standard TaqMan PCR Kit protocol on an Applied Biosystems 7900HT Sequence Detection System. The 10-μL PCR included 0.67 μL RT product, 1 μL TaqMan Universal PCR Master Mix (Applied Biosystems), 0.2 mM TaqMan probe, 1.5 mM forward primer, and 0.7 mM reverse primer. The reactions were incubated in a 96-well plate at 95° C. for 10 min, followed by 40 cycles of 95° C. for 15 s and 60° C. for 1 min. All reactions were run in triplicate. The threshold cycle (Ct) is defined as the fractional cycle number at which the fluorescence passes the fixed threshold. The comparative Ct method for relative quantification of gene expression (Applied Biosystems) was used to determine miRNA expression levels. The y axis represents the 2("ΔCt), or the relative expression of different miRs. MiRs expression was calculated relative to U44 and U48 rRNA. Experiments were carried out in triplicate for each data point, and data analysis was performed by using software (Bio-Rad).

Luciferase Assay.

To generate BCL2-like 11 (BIM) luciferase reporter constructs, the 3' UTR was amplified by PCR and cloned downstream of the luciferase-coding sequence in the pGL3-control vector at the XbaI restriction site (Promega). Mutations were introduced into the miRNA-binding sites by using the QuikChange Mutagenesis Kit (Stratagene). Meg-01 cells were transfected with Lipofectamine 2000 (Invitrogen), 1.2 μg of pGL3control containing BIM or BIM-UTR mutated 200 ng of Renilla luciferase expression construct (Promega). After 24 h, cells were lysed and assayed with Dual Luciferase Assay (Promega) according to the manufacturer's instructions.

To study the role of AP1 on miR-494 promoter, two (S1, S2) DNA fragments containing the putative regulatory region up-stream to miR-494 were amplified and cloned in pGL3basic (Promega). Meg01 cells were transfected with Lipofectamine 2000 (Invitrogen), 1.2 μg of pGL3basic empty vector or of pGL3 containing the above genomic fragments, 200 ng of Renilla luciferase expression construct pRL-TK (Promega) and ERK1/2, c-Jun, c-Fos siRNAs. After 24 h, cells were lysed and assayed with Dual Luciferase Assay (Promega) according to the manufacturer's instructions.

The primers used for the cloning were the following:

```
Bim 3' UTR fw:
                                            [SEQ ID NO: 1]
5' tctagaGAGCCAAATGTCTGTGTGCAA 3';
```

-continued

Bim 3' UTR rw:
[SEQ ID NO: 2]
5' tctagagagtgggagacagggatgttaat 3';

Bim mut fw:
[SEQ ID NO: 3]
5' CTG TGT GAT GTG TCC TAC TAA TGC TGT AAC
TTG TAG 3';

Bim mut rw:
[SEQ ID NO: 4]
5' CTACAAGTTACAGCATTAGTAGGACA-CATCACACAGT;

Pr494 1 FW:
[SEQ ID NO: 5]
5' GGTAC CTCA TCA TCC CCA CCT AAC GTA GC 3';

Pr494 1 RW:
[SEQ ID NO: 6]
5' AAGCTTCGTGAGAACACCAGTGAGA-GATG 3';

Pr494 2 Fw:
[SEQ ID NO: 8]
5' GGTACCGTC GAA GTC ATG CAT ATG CAT CG 3';
and

Pr494 2 Rw:
[SEQ ID NO: 9]
5' AAGCTTGGTAAATTGTAGTGCTGTGTTGCTC 3'.

Chromatin Immunoprecipitation.

Chromatin immunoprecipitation was performed. Cells ($5\times10^6$) from the 293A cell line were fixed in 1% formaldehyde for 10 min at 37° C. Cells were washed with ice-cold 1xPBS, scraped in 1xPBS plus protease inhibitors, and collected by centrifugation. Cell pellets, resuspended in cell lysis buffer (50 mmol/L Tris-HCl [pH 8.0], 10 mmol/L EDTA, and 1% SDS) plus protease inhibitors, were then sonicated. DNA-protein complexes were immunoprecipitated using 5 µg of the anti-c-Jun antibody (Santa Cruz) or with rabbit polyclonal IgG control (Zymed). Cross-links in the immunoprecipitated chromatin were reversed by heating with proteinase K at 65° C. overnight, and DNA was purified by the MinElute Reaction Cleanup column (Qiagen) and resuspended in water. The purified chromatin was subjected to PCR and the products were analyzed by gel electrophoresis using 2% agarose. The following primers were used:

S1 chip Fw:
[SEQ ID NO: 10]
5'ATG CATTAATTTAAAAGCTCTCAAATGGATG 3';

S1 chip Rw:
[SEQ ID NO: 11]
5' GACAAGAAATGGTCAGTGTGAGGCAT;

S2 chip Fw:
[SEQ ID NO: 12]
5' ATGATCGTTGTAGAGCATCAGGCCTT;

S2 chip Rw:
[SEQ ID NO: 13]
5' GATGAACTCTCAATTTGGATCAAACCCG 3';

C-ChIP FW"
[SEQ ID NO: 14]
5' GTT GGG TGG TTC ATT TAA GGG TAT TCC TGA 3';

C-ChIP RW:
[SEQ ID NO: 15]
5' TCATCAATGGGAGAATAATTTAATCAGCTC 3'.

Cell Death and Cell Proliferation Assay.

Cells were plated in 96-well plates in triplicate and incubated at 37° C. in a 5% $CO_2$ incubator. Super-Killer TRAIL (Alexis Biochemicals) was used as described herein. Viability of cells was examined with 3-(4,5-dimethylthiazol-2-yl)-2,5-diphenyltetrazolium bromide Cell Titer 96 AQueous One Solution Cell Proliferation Assay (Promega), according to the manufacturer's protocol. Metabolically active cells were detected by adding 20 µL to each well. After 1 h of incubation, the plates were analyzed in a Multilabel Counter (Bio-Rad Laboratories). Apoptosis was assessed using caspase 3/7 activity. Cells were seeded at $1.8\times10^6$ cells per 100 mm dish, grown overnight in 10% FBS/RPMI, washed with PBS, and then treated for 16 h with TRAIL 400 ng/mL for A549 and 200 ng/mL for H460. For detection of caspase 3/7 activity, cells were cultured in 96-well plates and treated with TRAIL 400 ng/mL for A549 and 200 ng/mL for H460 and analyzed using Caspase-Glo 3/7 Assay kit (Promega) according to the manufacturer's instructions. The percentage of caspase activity was corrected for backgrounds.

Generation of H460 Stable Clones With miR-494 Over-Expression and A549 Stable Clones With miR-494 Down-Regulation.

H460 cells were stably infected with the Human pre-miRNA Expression Construct Lenti-miR expression plasmid containing the full-length miR-494 and the GFP gene under the control of two different promoters (System Biosciences). An empty vector was used as control. A549 cells were stably infected with the Human anti-microRNA Expression Construct Lenti-miR expression plasmid containing the anti-miR-494 and the GFP gene under the control of two different promoters (System Biosciences). Pre-miR-494 and anti-miR-494 expression and control constructs were packaged with pPACKH1 Lentivector Packaging Plasmid mix (System Biosciences) in a 293TN packaging cell line. Viruses were concentrated using PEGit Virus Precipitation Solution, and titers were analyzed using the UltraRapid Lentiviral Titer Kit (System Biosciences). Infected cells were selected by FACS analysis (FACSCalibur; BD Bioscience). Infection efficiency>90% was verified by fluorescent microscopy and confirmed by real-time PCR for miRs expression.

Clonogenic Assay.

A total of 500 cells each (H460-Empty, H460miR-494, A549-Zip, A549-anti-miR-494) were seeded into 10-mm plates in sextuplicates. Two weeks later, the cells were stained and fixed and colonies were counted.

In Vivo Experiments.

Animal studies were performed according to institutional guidelines. H460-Empty, H460-miR-494, A549-Zip, and A549-anti-miR-494 stabled infected cells were used. $2\times10^6$ positive cells were injected s.c. into the right flanks of five 6-wk-old male nude mice (Charles River Breeding Laboratories). Tumor size was assessed every 2 d by a digital caliper. The tumor volumes were determined by measuring the length (l) and the width (w) and calculating the volume (V=l w/2). Thirty days after injection, mice were killed. Statistical significance between control and treated animals was evaluated by using Student t test Animal experiments were conducted after approval of the Institutional animal care and use committee, Ohio State University.

Further Examples

Therapeutic/Prophylactic Methods and Compositions

Further described herein are methods of treatment and prophylaxis by administration to a subject an effective amount of a therapeutic compound, i.e., a monoclonal (or polyclonal) antibody, viral vector, mimic and/or antagonist.

In a preferred aspect, the therapeutic is substantially purified. The subject is preferably an animal, including but not limited to, animals such as cows, pigs, chickens, etc., and is preferably a mammal, and most preferably human.

Various delivery systems are useful to administer a therapeutic compound, e.g., encapsulation in liposomes, microparticles, microcapsules, expression by recombinant cells, receptor-mediated endocytosis, construction of a therapeutic nucleic acid as part of a retroviral or other vector, etc. Methods of introduction include, but are not limited to, intradermal, intramuscular, intraperitoneal, intravenous, subcutaneous, intranasal, and oral routes. The therapeutic compounds are administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the therapeutic compositions locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, the implant being of a porous, non-porous, or gelatinous material, including membranes, such as sialastic membranes, or fibers. In one embodiment, administration is by direct injection at the site (or former site) of a malignant tumor or neoplastic or pre-neoplastic tissue.

In a specific embodiment where the therapeutic is a nucleic acid encoding a protein therapeutic the nucleic acid is administered in vivo to modulate expression of its encoded protein, by constructing it as part of an appropriate nucleic acid expression vector and administering it so that it becomes intracellular, or coating with lipids or cell-surface receptors or transfecting agents, or by administering it in linkage to a homeobox-like peptide which is known to enter the nucleus. Alternatively, a nucleic acid therapeutic can be introduced intracellularly and incorporated within host cell DNA for expression, by homologous recombination.

Pharmaceutical Compositions.

Such compositions comprise a therapeutically effective amount of a therapeutic, and a pharmaceutically acceptable carrier or excipient. Such a carrier includes, but is not limited to, saline, buffered saline, dextrose, water, glycerol, ethanol, and combinations thereof. The carrier and composition can be sterile. The formulation will suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In one embodiment, the composition is formulated in accordance with routine procedures as a pharmaceutical composition adapted for intravenous administration to human beings. For example, compositions for intravenous administration are solutions in sterile isotonic aqueous buffer. Where necessary, the composition also includes a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it is be dispensed with an infusion bottle containing sterile pharmaceutical grade water or saline. Where the composition is administered by injection, an ampoule of sterile water for injection or saline is provided so that the ingredients are mixed prior to administration.

The therapeutic formulation can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the therapeutic formulation which will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation will also depend on the route of administration, and the seriousness of the disease or disorder, and is decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems Method of Treating Cancer Patients This example describes a method of selecting and treating patients that are likely to have a favorable response to treatments with compositions herein.

A patient diagnosed with cancer ordinarily first undergoes tissue resection with an intent to cure. Tumor samples are obtained from the portion of the tissue removed from the patient. RNA is then isolated from the tissue samples using any appropriate method for extraction of small RNAs that are well known in the art, such as by using TRIZOL™. Purified RNA is then subjected to RT-PCR using primers specific for miR-494 or other differentially expressed miRNAs disclosed, optionally in conjunction with genetic analysis. These assays are run to determine the expression level of the pertinent RNA in the tumor. If differentially expressed miR expression pattern is determined, especially if mutant status is ascertained, the patient is evaluated as to whether the patient is a candidate for treatment with the compositions herein.

Accordingly, the patient is treated with a therapeutically effective amount of the compositions according to methods known in the art. The dose and dosing regimen of the compositions will vary depending on a variety of factors, such as health status of the patient and the stage of the cancer. Typically, treatment is administered in many doses over time.

Evaluation of miR levels at different periods of time may be used to determine appropriate dosage, changing therapeutics, ceasing treatment, or initiating a treatment regime.

Methods of Diagnosing Cancer Patients

In one particular aspect, there is provided herein a method of diagnosing whether a subject has, or is at risk for developing, cancer. The method generally includes measuring the differential miR expression pattern of the miR compared to control. If a differential miR expression pattern is ascertained, the results are indicative of the subject either having, or being at risk for developing, cancer. In certain embodiments, the level of the at least one gene product is measured using Northern blot analysis. Also, in certain embodiments, the level of the at least one gene product in the test sample is less than the level of the corresponding miR gene product in the control sample, and/or the level of the at least one miR gene product in the test sample is greater than the level of the corresponding miR gene product in the control sample.

In some embodiments, mRNA-containing samples may be obtained from, blood, mucus, sputum, bronchoscopic biopsy, needle biopsy, open biopsy, or video-assisted thoracoscopic surgery.

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, lung cancer, particularly EGFR mutant lung cancer.

Diagnostic and Therapeutic Applications

In another aspect, provided herein are methods of treating a cancer in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a cancer associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Kits

Also provided are pharmaceutical packs or kits comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of the sequences herein.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method to inhibit down-regulation of Bcl-2-like protein 11 (BIM) in a TRAIL-resistant cancer cell that over-expresses miR-494, comprising administering an effective amount of at least one inhibitor of miR-494 to the cancer cell and inhibiting BIM down-regulation.

2. The method of claim 1, wherein the cancer is selected from the group consisting of: lung cancer, breast cancer, osteosarcoma, gastrointestinal tumors and melanoma.

3. The method of claim 1, further comprising:
measuring a miR-494 expression level in the cancer cell prior to administering TRAIL and anti-miR-494;
classifying the cancer cell as over-expressing miR-494 if the miR-494 level is is 2-12 fold higher than a control level; and
administering the inhibitor of miR-494 in an amount sufficient to reduce miR-494 levels; wherein the miR-494 level is reduced by at least 25%.

* * * * *